(12) United States Patent
Krasnow et al.

(10) Patent No.: US 10,942,163 B1
(45) Date of Patent: *Mar. 9, 2021

(54) SYSTEM AND METHOD FOR METERING, DISPENSING, FILTERING, AND MIXING MICRO-VOLUMES OF FLUIDS

(71) Applicant: Verily Life Sciences LLC, Mountain View, CA (US)

(72) Inventors: Benjamin David Krasnow, Redwood City, CA (US); Eric Peeters, San Jose, CA (US); Peter Howard Smith, Pacifica, CA (US); Ethan Glassman, Palo Alto, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 866 days.

This patent is subject to a terminal disclaimer.

(21) Appl. No.: 15/648,906

(22) Filed: Jul. 13, 2017

Related U.S. Application Data

(60) Provisional application No. 62/367,990, filed on Jul. 28, 2016.

(51) Int. Cl.
*G01N 33/487* (2006.01)
*G01N 33/00* (2006.01)
(Continued)

(52) U.S. Cl.
CPC .......... *G01N 33/4875* (2013.01); *G01N 1/10* (2013.01); *G01N 1/28* (2013.01); *G01N 33/0067* (2013.01); *G01N 33/487* (2013.01); *G01N 33/50* (2013.01); *G01N 33/5008* (2013.01); *G01N 2001/387* (2013.01)

(58) Field of Classification Search
CPC .......... A61B 5/150022; A61B 5/15115; A61B 5/150412; A61B 5/15151; A61B 5/15163; A61B 5/681; A61B 5/15003; A61M 2005/206; G01N 15/05; G01N 2015/0065; G01N 33/49
See application file for complete search history.

(56) References Cited

U.S. PATENT DOCUMENTS 9,730,625 B2 * 8/2017 Krasnow .......... A61B 5/150099
2015/0110721 A1 * 4/2015 Conrad ................ A61B 5/0071
424/9.34

* cited by examiner

*Primary Examiner* — Lyle Alexander
*Assistant Examiner* — Bryan Kilpatrick
(74) *Attorney, Agent, or Firm* — Kilpatrick Townsend & Stockton LLP

(57) ABSTRACT

Devices for micro-fluid mixing micro-fluids are presented, together with example methods for micro-mixing using example devices. An example device may include a micro-volume fluid chamber (μVFC), a micro-volume mixing chamber (μVMC), and a source of a target micro fluid. The μVFC may include two slidably-mounted piston segments that divide the μVFC into three sub-volumes, one of which initially contains a mixer micro-fluid. The source of the target micro fluid may be triggered to deliver the target micro-fluid into another of the sub-volumes via an inlet channel. A propellant may be triggered to drive axial motion of the piston segments, causing the sub-volumes to compress. Through this action, the mixer micro-fluid may be expelled via a first outlet channel into the μVMC, and the target micro-fluid may be expelled via a second outlet channel into the μVMC. As the piston segments move, they block and unblock the inlet and outlet channels.

39 Claims, 12 Drawing Sheets

(51) Int. Cl.
*G01N 33/50* (2006.01)
*G01N 1/38* (2006.01)
*G01N 1/10* (2006.01)
*G01N 1/28* (2006.01)

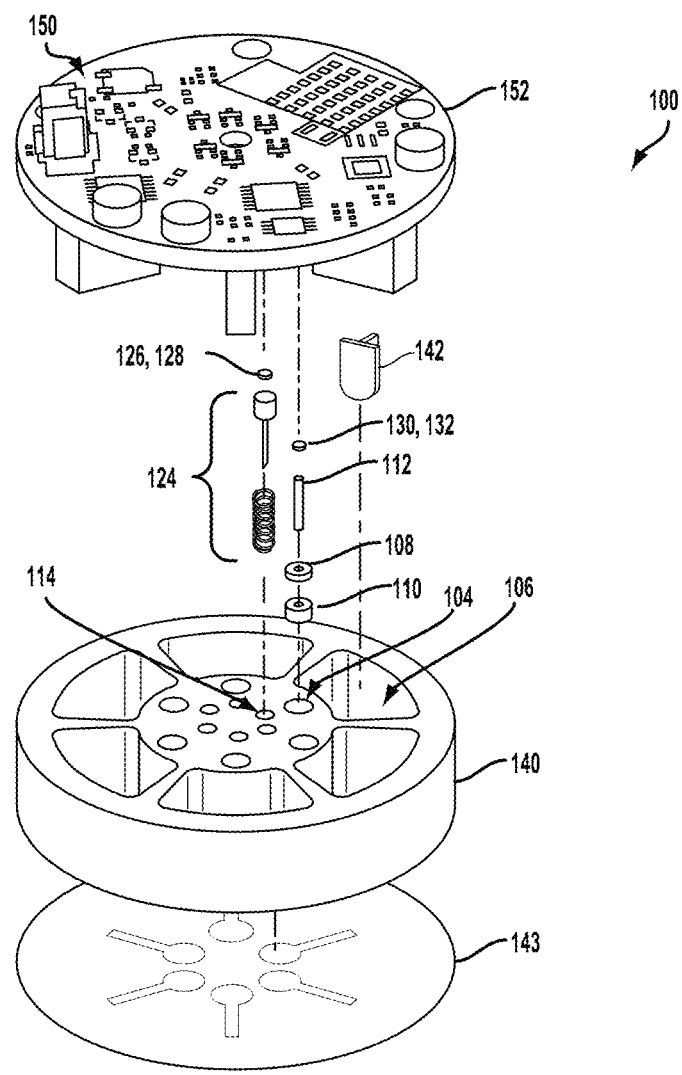
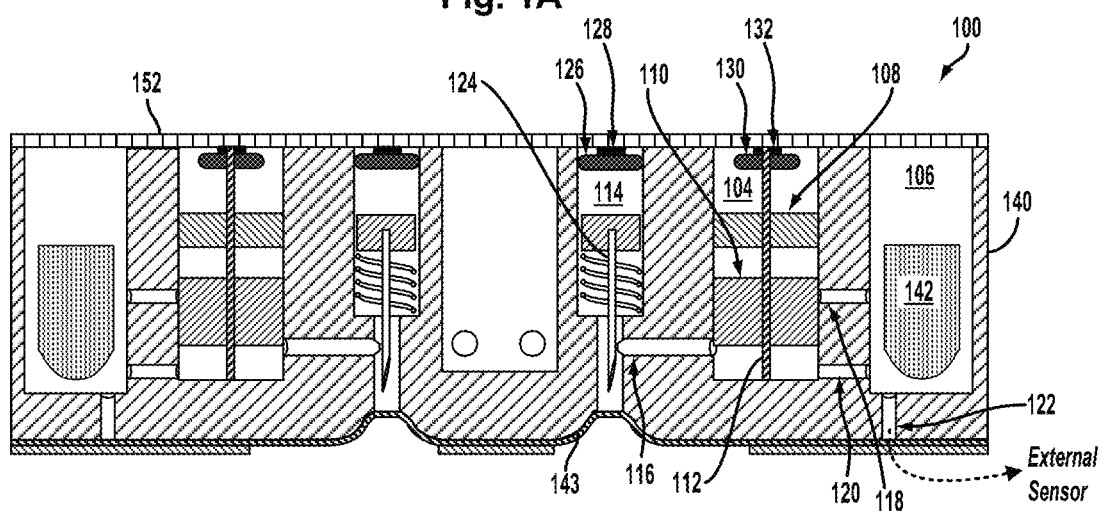
Fig. 1A
Fig. 1B

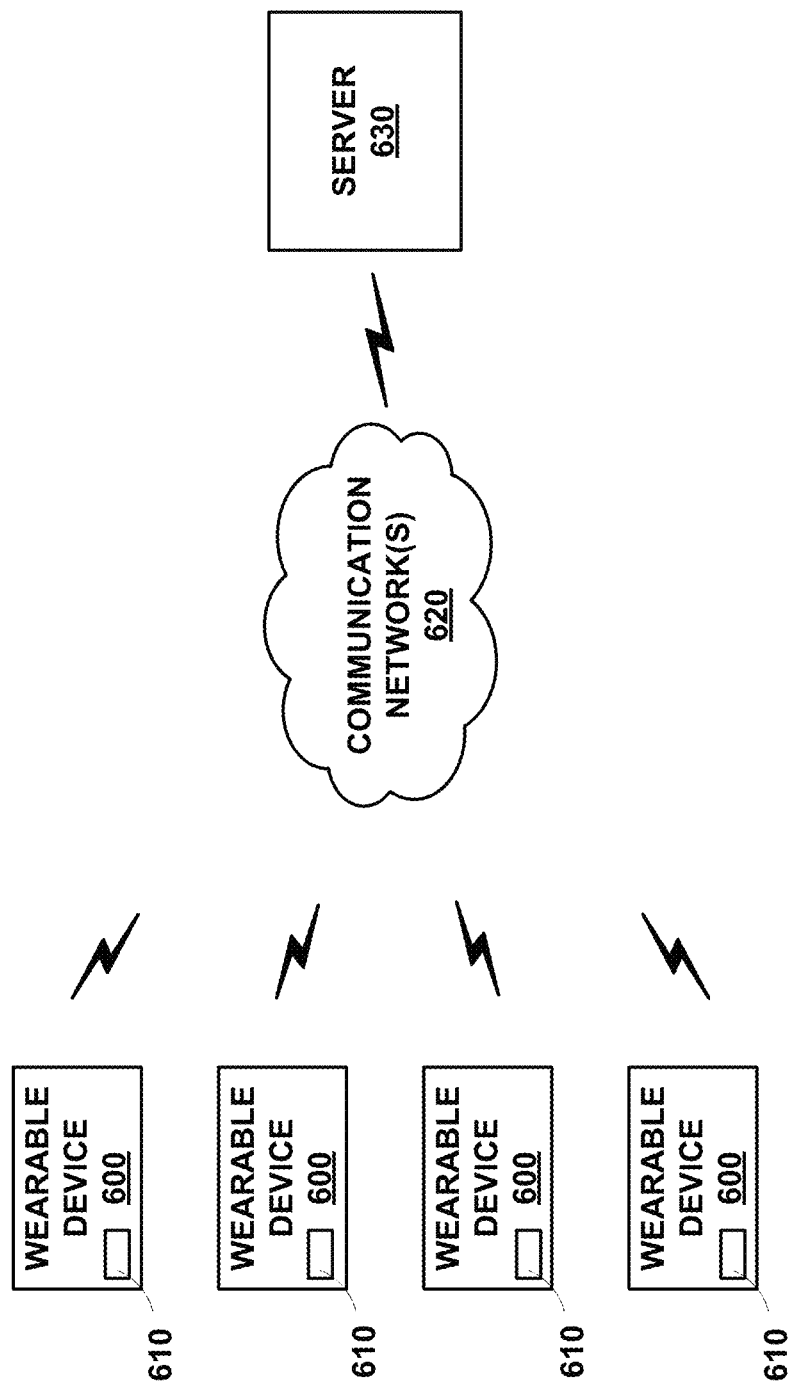

SYSTEM AND METHOD FOR METERING, DISPENSING, FILTERING, AND MIXING MICRO-VOLUMES OF FLUIDS

CROSS-REFERENCE TO RELATED APPLICATIONS

This application claims priority under 35 U.S.C. § 119(e) to U.S. Provisional Patent Application Ser. No. 62/367,990, filed on Jul. 28, 2016, which is incorporated herein in its entirety by reference.

BACKGROUND

Unless otherwise indicated herein, the materials described in this section are not prior art to the claims in this application and are not admitted to be prior art by inclusion in this section.

Certain medical states or conditions of a human body can be detected by detecting one or more properties of blood in the body. In some examples, such medical states can be detected by extracting a sample of the blood from the body and detecting the one or more properties of the extracted blood using a sensor or other system external to the body. For example, a lancet or other skin-penetrating device could be used to penetrate the skin such that blood is emitted from the skin and/or such that blood can be caused to be emitted from the skin. In another example, a needle, tubing, and other equipment could be used to access blood in an artery or vein of a body. Blood accessed from a body can be exposed to a sensor (e.g., a sensor placed in contact with blood at the surface of skin that has been penetrated). Additionally or alternatively, accessed blood can be stored for later analysis. In a particular example, a lancet can be used to penetrate skin, allowing blood to be emitted from the skin such that a blood glucose level of the blood can be measured using an electrochemical sensor placed in contact with the emitted blood. For some types of analysis, drawn blood may be mixed with one or more other fluids. Accordingly, technologies for fluid mixing may play a role in blood testing, among other applications.

SUMMARY

Some embodiments of the present disclosure provide a micro-fluid mixing device including a micro-cylinder block housing a hydraulic micro-volume cylinder chamber (HμVCC) and a micro-volume mixing chamber (μVMC), the HμVCC and μVMC both having respective interior volumes in a range of 1-100 microliters. The micro-fluid mixing device further includes a piston assembly slidably accommodated in the HμVCC for motion along an axial direction of the HμVCC, a source of pressurized gas having a triggered release mechanism, a micro-fluid inlet in the micro-cylinder block comprising a micro-fluid inlet channel providing a fluid connection from a source of a target micro-fluid to an inlet port in an interior wall of the HμVCC, a first micro-fluid outlet in the micro-cylinder block comprising a first micro-fluid outlet channel providing a fluid connection from a first outlet port in the interior wall of the HμVCC to a first inlet opening in an interior wall of the μVMC, and a second micro-fluid outlet in the micro-cylinder block comprising a second micro-fluid outlet channel providing a fluid connection from a second outlet port in the interior wall of the HμVCC to a second inlet opening in the interior wall of the μVMC. The piston assembly includes (i) a top segment (TS) axially slidable from a TS initial position to a TS final position, and, beneath the TS, (ii) a bottom segment (BS) axially slidable from a BS initial position to a BS final position, wherein the TS and BS divide the interior volume of the HμVCC into a top sub-volume extending above the TS to a top of the HμVCC, a middle sub-volume between the TS and BS, and a bottom sub-volume extending beneath the BS to a floor of the HμVCC. The size and axial position of each sub-volume are adjustable according to the axial positions of the TS and BS within the HμVCC. The a source of pressurized gas is dynamically coupled into the top sub-volume. With the TS in the TS initial position and the BS in the BS initial position, at least: (i) all three sub-volumes are non-zero and positive, each defining a respective initial sub-volume, (ii) the middle sub-volume is filled with an initial mixer volume of mixer micro-fluid that hydraulically links slidable motion of the TS and BS, (iii) the first outlet port is blocked by the BS, and (iv) the inlet port and the second outlet port are both at least partially unobstructed, the inlet port being open to fluid flow from the source of the target micro-fluid into the bottom sub-volume, and the second outlet port being open to fluid flow from the bottom sub-volume into the μVMC. With the TS in at least one intermediate position between the TS initial position and the TS final position and the BS in at least one intermediate position between the BS initial position and the BS final position, at least: (i) the first outlet port is at least partially unobstructed, the first outlet port being open to fluid flow from the middle sub-volume to the μVMC. With the TS in the TS final position and the BS in the BS final position, at least: (i) the middle sub-volume is zero, (ii) the first outlet port is blocked by the TS, (iii) the bottom sub-volume is substantially zero, and (iv) the inlet port and the second outlet port are blocked by the BS. The source of pressurized gas, upon triggered release into the top sub-volume, provides sufficient pressure force to drive motion of the TS and BS from the respective TS and BS initial positions to the respective TS and BS final positions.

Some embodiments of the present disclosure provide a method employing a micro-cylinder block housing a hydraulic micro-volume cylinder chamber (HμVCC) and a micro-volume mixing chamber (μVMC), the HμVCC and μVMC both having respective interior volumes in a range of 1-100 microliters. The method comprises mounting a piston assembly slidably in the HμVCC for motion along an axial direction of the HμVCC, wherein the piston assembly comprises (i) a top segment (TS) axially slidable from a TS initial position to a TS final position, and, beneath the TS, (ii) a bottom segment (BS) axially slidable from a BS initial position to a BS final position, and wherein the TS and BS divide the interior volume of the HμVCC into a top sub-volume extending above the TS to a top of the HμVCC, a middle sub-volume between the TS and BS, and a bottom sub-volume extending beneath the BS to a floor of the HμVCC, the size and axial position of each sub-volume being adjustable according to the axial positions of the TS and BS within the HμVCC. The method further comprises positioning the TS in the TS initial position and the BS in the BS initial position with the middle sub-volume filled with an initial mixer volume of mixer micro-fluid that hydraulically links slidable motion of the TS and BS, wherein with the TS in the TS initial position and the BS in the BS initial position, at least: (i) all three sub-volumes are non-zero and positive, each defining a respective initial sub-volume, (ii) a first outlet port in an interior wall of the HμVCC to a first fluid connection to the μVMC is blocked by the BS, (iii) an inlet port in the interior wall of the HμVCC from a source of a target micro-fluid is at least partially unobstructed, such that the inlet port is open to fluid flow from the source of the target micro-fluid into the bottom sub-volume, and (iv) a second outlet port in the interior wall of the HµVCC to a second fluid connection to the µVMC is at least partially unobstructed, such that the second outlet port is open to fluid flow from the bottom sub-volume into the µVMC. The method further comprises triggering release of the target micro-fluid from the source of the target micro-fluid to the inlet port while the inlet port is open to fluid flow from the source of the target micro-fluid into the bottom sub-volume. The method further comprises while the TS is in the TS initial position and the BS is in the BS initial position, triggering delivery of pressurized gas into the top sub-volume with sufficient pressure force to drive motion of the TS and BS from their respective TS and BS initial positions to their respective TS and BS final positions, wherein with the TS in the TS final position and the BS in the BS final position, at least: (i) the middle sub-volume is zero, (ii) the first outlet port is blocked by the TS, (iii) the bottom sub-volume is substantially zero, and (iv) the inlet port and the second outlet port are blocked by the BS. The method further comprises during the motion of the TS and BS from their respective TS and BS initial positions to their respective TS and BS final positions, receiving a target volume of the target micro-fluid into the bottom sub-volume through the inlet port. The method further comprises during the motion of the TS and BS from their respective TS and BS initial positions to their respective TS and BS final positions, expelling the target volume of the target micro-fluid from the bottom sub-volume into the µVMC through the second outlet port by pressure of the BS moving toward the BS final position. The method further comprises during the motion of the TS and BS from their respective TS and BS initial positions to their respective TS and BS final positions, unblocking the first outlet port by motion of the BS toward the BS final position, such that the first outlet port becomes at least partially unobstructed by the BS. And the method further comprises during the motion of the TS and BS from their respective TS and BS initial positions to their respective TS and BS final positions, while the first outlet port is at least partially unobstructed by the BS, expelling the initial mixer volume of the mixer micro-fluid from the middle sub-volume into the µVMC through the first outlet port by pressure of the TS moving toward the BS.

Some embodiments of the present disclosure provide a micro-fluid mixing device including a micro-vessel block housing both a plurality of micro-volume fluid chambers (µVFCs) and a micro-volume mixing chamber (µVMC), the µVFCs and µVMC each having respective interior volumes in a range of 1-100 microliters. The a micro-fluid mixing device further includes a respective micro-fluid outlet channel between each respective µVFC and the µVMC, each respective micro-fluid outlet channel providing a respective fluid connection from a respective outlet port in the respective µVFC to a respective inlet opening in the µVMC, a respective deformable interior surface portion in each respective µVFC for reducing a respective interior volume of the respective µVFC from a respective initial volume to a smaller, respective final volume according to deformation of the respective deformable interior surface portion from a respective initial position to a respective final position, a respective micro-fluid filling the respective initial volume of each respective µVFC and a source of pressurized gas having a triggered release mechanism and being dynamically coupled to an exterior surface of each respective deformable interior surface portion, and comprising a source of sufficient pressure force for expelling the respective micro-fluid from each respective µVFC into the µVMC via the respective micro-fluid outlet channels by deforming each respective deformable interior surface portion from its respective initial position to its respective final position.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 1A is an exploded view of an example device.
FIG. 1B is a cross-sectional view of the example device of FIG. 1A.
FIG. 6 is a block diagram of an example system that includes a plurality of wearable devices in communication with a server.

DETAILED DESCRIPTION

Figure 2A:
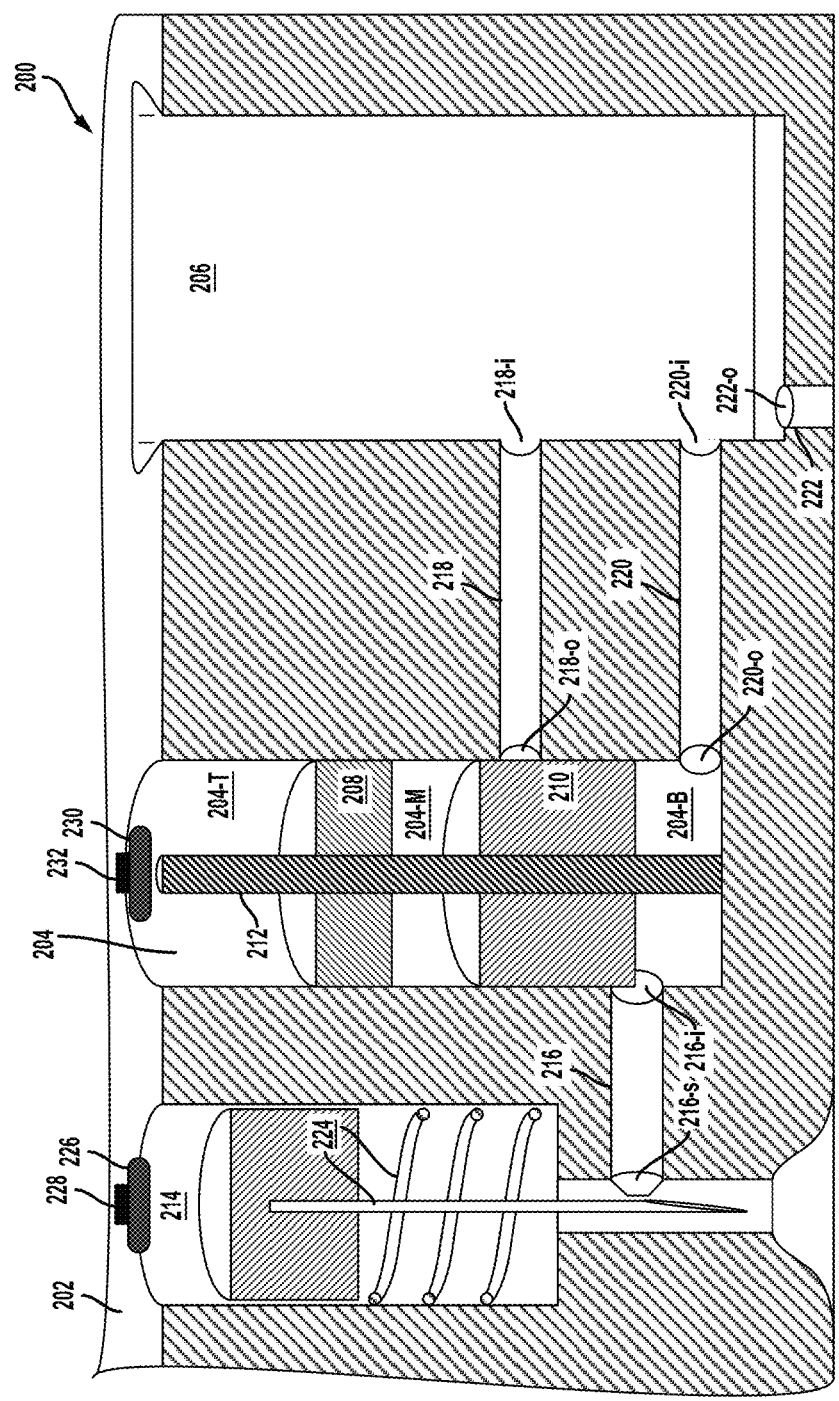
FIG. 2A is a cross-sectional view of an example device.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Further, while embodiments disclosed herein make reference to use on or in conjunction with a living human body, it is contemplated that the disclosed methods, systems and devices may be used in any environment where the operation of a device to extract a fluid from an environment of interest by piercing a barrier and/or penetrating an element within the environment of interest is desired. The environment may be or include any living or non-living body or a portion thereof, a gel, an emulsion, a fluid conduit, a fluid reservoir, etc.

I. Overview

Some types of testing and analysis and other forms of processing of fluids involve mixing very small volumes of fluids—volumes characterized roughly by a few to tens of microliters. In these small quantities, a fluid is referred to as a "micro-fluid." Applications of micro-fluid processing may need to employ micro-fluid devices that can easily measure, mix and dispense micro-fluids to achieve a chemical test result or create a chemical product that is more useful or suitable for testing than its components. For example, in certain blood tests, a blood sample must be quantified, mixed with a reagent or diluent, filtered, and then administered or applied to a paper-based test strip or the like. Conventional laboratory blood-handling machines may include are numerous pumps, flowmeters, vacuum sensors, optical sensors, among other components, to control the process and ensure consistency. The bulkiness of conventional machines and components precludes the ability to miniaturize the blood testing machine into something that could be small enough and low-cost enough to be wearable or usable at home. More generally, conventional techniques for fluid mixing and processing typically employ devices too large to be suitable for micro-fluid applications, particularly those which call for miniaturization of components. Accordingly, example embodiments disclosed herein provide an example micro-fluid device and technique for metering, dispensing, filtering, and mixing micro-volumes of fluids.

In accordance with example embodiments, a micro-fluid mixing device may include two or more "micro-volume" fluid chambers for holding respective micro-fluids, and a micro-volume mixing chamber into which the two or more micro-fluids may be dispensed from the fluid chambers, and mixed in preparation for testing or chemical analysis, or other processing. For the purposes of the discussion herein, the term "micro-volume" will be used to refer to volumes in a range of 1-100 microliters, and the term "micro-fluid" will be used to refer to a micro-volume amount or quantity of a fluid. The term "micro-fluid mixing" will be used to refer to mixing of two or more micro-fluids. Thus, a "micro-fluid mixing device" is a device in accordance with example embodiments for micro-fluid mixing (as well as other possible processing of micro-fluids). Further, the terms "miniature," "miniaturized," and "miniaturization" will be used herein to characterize the size of a micro-fluid mixing device or a micro-volume-sized subsystem of a device, which itself may or may not be miniature.

In one example device, the micro-volume fluid chambers ("μVFCs") and the micro-volume mixing chamber ("μVMC") may be housed in a micro-vessel block. Each μVFC may have a respective micro-fluid outlet channel that provides a respective fluid connection from a respective outlet port in the respective μVFC to a respective inlet opening in the μVMC. Further, each μVFC may have a respective deformable interior surface portion that can be deformed from an initial position to a final position. In doing so, the interior volume of the respective μVFC may be reduced from an initial volume to a smaller, final volume. By filling the initial volume of each μVFC with a respective micro-fluid, the action of deforming the deformable surface portions can then force the expulsion of each micro-fluid from the respective μVFC into the μVMC. More particularly, the example micro-fluid mixing device may further include a source of pressurized gas that can be triggered to drive the deformation, and therefore the dispensing (expulsion) and mixing of the micro-fluids. In one aspect of this example, the initial volume of a particular one of the μVFCs may be filled with a target micro-fluid supplied dynamically (e.g., in a triggered action) by a source having a fluid connection into the particular μVFC, while the others may be preconfigured to contain initial volumes of respective micro-fluids.

In another example device, a hydraulic micro-volume cylinder chamber ("HμVCC") and aμVMC may be housed in a micro-cylinder block. More particularly, an axial piston assembly having piston segments arranged axially can be fitted slidably in the HμVCC so that the piston segments sub-divide the interior volume of the HμVCC into the sub-volumes, one or more of which may initially be filled with a micro-fluid. Two or more micro-fluid outlet channels provide respective fluid connections from respective outlet ports in the interior wall of the HμVCC to respective inlet openings in the μVMC. Axial motion of the piston segments from initial to final positions cause them to traverse the various outlet ports, blocking (closing) and/or unblocking (opening) the outlet ports in the process. At the same time, the sub-volumes move with the sliding motion of the piston segments, thereby coming to encompass one or another open outlet, and/or coming to have an open outlet become block, as a function of motion and position of the piston segments. When a micro-fluid-filled sub-volume encompass an open outlet, the contained micro-fluid may then be expelled into the μVMC by pressure of the moving piston segments. The sliding motion of the piston segments may also reduce the sub-volumes from initial to final size as contained micro-fluids are compressively expelled.

In one example using the multi-segment piston assembly, the piston assembly has two segments: a top segment (TS) and bottom segment (BS). In their initial positions, TS and BS sub-divide the interior volume of the HμVCC into three sub-volumes: top, middle, and bottom. The middle sub-volume may be filled with a "mixing" micro-fluid, while the bottom sub-volume may have micro-fluid inlet channel providing a fluid connection from a source of a "target" micro-fluid to an inlet port in the interior wall of the HμVCC. Also in their initial positions, a first outlet port in the bottom sub-volume may be open, while a second outlet port in the axial-motion path of the middle sub-volume is close—sealed by the BS. In operation, the target micro-fluid may be delivered dynamically from the source into the bottom sub-volume. Axial motion of the TS and BS may be triggered by pressurized gas coupled into the top sub-volume. Thereafter, as the piston segments move toward their final positions, the second outlet port will open causing the mixing fluid expelled into the μVMC by pressure of the middle sub-volume shrinking as the TS moves toward the BS. Similarly, the target fluid will be expelled into the μVMC by pressure of the bottom sub-volume shrinking as the BS moves toward its final position. Depending on the placement of the first and second outlets, the relative thickness of the TS and BS, and relative timing of target micro-fluid delivery and triggered motion of the piston segments, the target and mixer micro-fluids can be expelled into the μVMC sequentially (in either one of two orders) or concurrently.

For purposes of illustration, example embodiments of a micro-fluid mixing device will be described herein primarily in the context of a miniaturized blood testing machine or apparatus, in which case the target fluid could be blood, and the source of the target fluid could be a blood-drawing subsystem. A miniaturized blood testing machine can be part of a wearable or portable device arranged for drawing a small amount (e.g., micro-volume) of blood and carrying out one or more test on the drawn blood. The ability to test with a micro-volume of blood may have an added benefit of enabling a nearly (or entirely) pain-free blood-drawing operation. For example, using an extremely thin needle or employing a needle-free technique can allow piercing or puncturing the skin to be imperceptible. However, it can also result in the volume of blood drawn being sufficiently small as to make testing difficult. A pain-free blood draw might yield 10-20 microliters of blood or less, for example. This may be too small an amount for certain blood tests.

As an example, some blood tests utilize a fibrous strip that wicks blood from one end of the strip to the other. As the blood travels through the strip, a colored line may appear to indicate a positive test result, for example. These tests are known as lateral-flow immunoassay (LFIA), and are often designed to detect large molecules like troponin (a cardiac biomarker), CK-MB (another cardiac marker), CRP (a general inflammatory indicator), and other chemicals. Typical LFIA tests designed for blood require 60 microliters or more of fluid for sufficient wicking across the strip. Thus, 10-20 microliters of blood or less from a tiny painless blood draw site is insufficient. However, mixing a smaller quantity of blood with diluent can allow the test can be run reliably, and the use of the diluent can compensate for the lower blood volume by multiplying the end results by a known factor. This approach is useful for any blood test that requires a relatively high volume and can tolerate dilution. Thus, one of the challenges for miniaturizing a blood testing machine is to incorporate miniaturized micro-mixing of a micro-volume of blood with a micro-volume of diluent in preparation for LIFA testing or the like.

As another example, some types of blood tests use an electrochemical sensor to detect and measure various ionic concentrations in the blood. Such test may be used, for instance, to measure sodium, potassium, and/or calcium concentrations, as well as pH. In practice, electrochemical sensors may need to be calibrated prior to exposure to blood in order to properly interpret sensor values measured for the blood. Calibration may be achieved by exposing (e.g., measuring) the sensor to a calibration fluid having known electrochemical properties. Doing so calibrates sensor measurements with the known or expected results, and thereby calibrates measurements taken subsequently for the blood. In an example miniaturized blood testing apparatus including a miniature electrochemical sensor, micro-fluid mixing can be used to direct a calibration micro-fluid to a sensor prior to directing a micro-volume of blood from a tiny blood draw to the sensor. The sensor may thus be calibrated in preparation for receiving and testing the micro-volume of blood.

It will be appreciated that micro-fluid mixing devices in accordance with example embodiments herein can have applications for miniaturization of micro-fluid mixing besides blood and/or medical fluid testing. The emphasis herein on example miniaturized blood testing devices serves a dual purpose of highlighting advantages specific to miniaturized blood testing, as well as providing useful contexts for describing example micro-mixing devices and techniques more generally and for other purposes.

In one example, a miniaturized blood testing machine could be a wearable device, having a form factor akin to a wrist watch. The wearable device could include a plurality of micro-cylinder blocks, each housing a HμVCC with a piston assembly, aμVMC, and other components and elements described above. Each could have a respective blood-drawing subsystem, such as triggered needle device for momentarily puncturing adjacent skin, drawing resultantly-emerging blood, and channeling it into one of the initial sub-volumes in a respective HμVCC. Triggered release of pressurized gas could then drive axial motion of the piston segments, causing the blood and a mixing fluid, in another sub-volume, to be expelled together into the μVMC, where they can mix and be applied to miniature blood-testing strip or other miniature blood-testing device or element. In an example where the mixing fluid is a calibration micro-fluid, the piston segments and outlet channels can be arranged so that the calibration micro-fluid expelled into the μVMC first, calibrating an electrochemical sensor before the drawn blood is expelled into the μVMC for measurement by the calibrated electrochemical sensor.

The wearable device could further include electronic components for controlling operation. For example, a microprocessor or the like could cause triggering of the blood-drawing device, as well as triggering release of the pressurized gas source for driving piston motion. It could also read and store results of blood testing and/or cause results to be transmitted to a server, for example. Further, the microcontroller could invoke testing action for a plurality of testing subsystems on a schedule, such as one or twice per day.

More generally, a body-mountable, wearable, handheld, desktop, or otherwise-configured device may be configured to access blood within a living body (or to access some other fluid in some other environment of interest). Such a blood-accessing device could include means for penetrating or piercing the skin to allow the blood to be emitted from the skin. Such penetrating or piercing means could include one or more needles driven into the skin by an injector incorporating chemical propellants, mechanical or electromechanical elements, or some other elements or components configured to drive the one or more needles into the skin and subsequently to retract the one or more needles from the skin to allow blood to be emitted from the skin via one or more punctures or other penetrations in the skin formed by the one or more needles. Such a blood-accessing device could additionally include suction means for applying suction, through one or more formed holes in a seal, to draw blood a micro-fluid mixing subsystem of the device, where the blood can be mixed with another micro-fluid, such as a reagent of diluent. The mixture can then be measured, detected, collected, stored, or otherwise used for some application. For example, the micro-volume mixing chamber of the device could include a sensor configured to detect glucose in blood received by the device from the skin. Additionally or alternatively, the needle driven into the skin could be a hollow needle, and suction could be applied through the hollow needle to draw blood into the device, through the hollow needle, when the needle is penetrating the skin. A body-mountable blood-mixing device could include multiple needles, injectors, seals, suction sources, sensors, micro-fluid storage elements, or other components such that the body-mountable blood-accessing device could be operated to automatically access blood from a wearer at a number of specified points in time, e.g., while the wearer sleeps.

Blood could be accessed by devices and systems described herein for a variety of applications. Upon or after mixing blood with one or more micro-fluids, one or more properties of blood mixture could be measured or detected. For example, a viscosity of the blood mixture, a concentration or state of one or more analytes in the blood mixture, or some other property of the blood mixture could be detected. For example, a concentration of glucose, of insulin, of one or more hormones, or of some other substance could be detected. Such analytes, and detected concentrations or other properties thereof, could be related to a health state of a person and could be used to determine such a health state. Further, such determined health states could be used to determine and/or indicate some medical or other action to be taken, for example, to take a dose of medicine (e.g., insulin), to perform an exercise, to seek medical attention, or some other action. Additionally or alternatively, detected analyte concentrations or other properties of a blood accessed and mixed at a plurality of points in time could allow for the determination of one or more physiological baselines or other physiological properties of a person (e.g., a baseline blood glucose concentration, a baseline daily blood glucose profile) and/or the determination and/or modification of a medical treatment regimen (e.g., a timing, dosage, or other property of application of a drug to a person).

An injector or other means configured to drive one or more needles or other means for penetrating skin could be configured in a variety of ways to provide a force to drive the one or more needles into the skin and subsequently retract the one or more needles. For example, the injector could include a piston disposed in a chamber and to which the one or more needles are coupled; a propellant could be used to apply pressure behind the piston to drive the piston, and attached one or more needles, forward such that the one or more needles are driven into the skin. A spring or other means could also be provided to apply a force to retract the one or more needles subsequent to being driven into the skin. In a particular example, the propellant could include a chemical or other material (e.g., nitrocellulose) that could be ignited (e.g., by being heated to an ignition temperature by, e.g., a resistive heating element) to produce gases that could apply pressure on the piston to drive the needle into skin. In another example, the propellant could include compressed gases introduced into the chamber (e.g., by opening a valve, by puncturing a seal, by electrochemically generating the gases, by chemically generating the gases) and the compressed gases could apply pressure on the piston to drive the needle into skin. Additionally or alternatively, an injector could include preloaded springs, magnetic elements coupled to cams, motors, solenoids, ultrasonic vibrators, or other elements configured to drive one or more needles into skin.

A suction source or other suction means configured to provide suction to a seal and to draw blood through one or more holes formed in such a seal (e.g., by one or more needles being driven through the seal) and/or to draw blood into a device by some other means (e.g., through a hollow needle) could provide suction by a variety of mechanisms. In some examples, the suction source could include a pump, an endobaric chemical process, a spring-loaded volume, or some other actuated element(s) configured to be operated to reduce a pressure to which the seal is exposed or to otherwise provide suction to the seal. In some examples, the suction source could include an evacuated volume, i.e., an enclosed volume having a lower pressure than the atmosphere surrounding the device such that, when the seal is breached, blood (or some other fluid or material) is drawn through/toward the one or more holes in the seal.

Such suction provided to a seal and/or through one or more holes formed in the seal could act to draw the skin toward the seal. In some examples, the device could include a concave depression (e.g., a spherical dome depression) formed in the seal and/or in some other element(s) of the device such that the suction provided by the suction source could draw a portion of the skin into the concave depression. Such displacement of the skin could act to increase a rate and/or duration of the emission of blood from the skin. A blood-accessing device could additionally or alternatively be configured in other ways to increase the rate and/or duration of the emission of blood from the skin following penetration by one or more needles. In some examples, heparin or some other anti-clotting or anti-coagulating substance could be introduced on/in the skin (e.g., by being deposited and/or injected by the one or more needles). In some examples, an amount of blood flow in the skin could be increased by, e.g., applying suction to the skin (e.g., using the same or a different suction source as is used to drawn blood through the seal), applying a frictive force to the skin (e.g., by rubbing the skin), and/or heating the skin before driving the one or more needles into the skin.

Blood accessed and mixed with one more micro-fluids by devices as described herein (e.g., by driving one or more needles into skin and applying suction to the skin to draw blood out of the skin and into the device) could be used for a variety of applications. In some examples, the device could contain a sensor that could be configured to detect one or more properties of the blood mixture (e.g., to detect the concentration of an analyte in the blood). Such sensors could operate based on contact between the blood and one or more elements of the sensors (e.g., an electrode of an electrochemical sensor). Alternatively, such sensors could be non-contact sensors (e.g., colorimetric or other optical sensors). Sensors could be configured to detect glucose, blood cell counts, electrolytes, hormones, cholesterol, or some other analytes in accessed blood.

Additionally or alternatively, devices as described herein could be configured to store a blood mixture for later use, e.g., for interrogation by sensors or other elements of some other devices or systems. For example, devices could access blood from skin, micro-mix the blood with one or more micro-fluids, and store the blood mixture; later, the stored blood mixture could be presented to a desktop sensor device or to some other system configured to receive the stored blood mixture and to detect one or more properties of the provided blood mixture. By appropriately accounting for properties of the mixture, properties of the blood itself could be determined. Storing a blood mixture could include providing heparin or other stabilizing and/or anti-clotting agents such that the blood is stored as a fluid. In some examples, one or more blood-storing elements of a blood access and mixing device could be removable, and could be removed from the device to be presented to another system for analysis (e.g., the removable blood-storing aspects of the device could be removed and sent to a centrally located laboratory).

In some examples, a blood-accessing and micro-mixing device may include a user interface that is configured to provide user-discernible indications (e.g., visual, audible, and/or tactile indications) of the operation of the device to access and micro-mix blood and/or information about accessed blood sensed by sensors of the device, progress or other information related to a function of the device, or other information. In some examples, the user interface could additionally provide a means for one or more settings of the device (e.g., timing of one or more future activations of the device to access and mix blood from skin, a user information privacy setting, a user's credentials to access a service) to be specified by a user according to the user's preferences. In some examples, the device may include a wireless communication interface that can transmit/receive data to/from an external device, for example, using Bluetooth, ZigBee, WiFi, and/or some other wireless communication protocol. The data transmitted by the wireless communication interface may include data indicative of one or more physiological parameters or health state measured and/or determined based on blood accessed by the device. The wireless communications interface could additionally or alternatively be configured to receive data from an external system.

It should be understood that the above embodiments, and other embodiments described herein, are provided for explanatory purposes, and are not intended to be limiting. Further, the terms "access," "accessed," "accessing," and any related terms used in relation to the operation of a device to induce emission of blood from skin are used herein (unless otherwise specified) to describe any operation or configuration of a device or system to receive blood from skin or from some other tissue. This could include receiving blood that has been emitted from skin in response to cutting, piercing, incising, cutting, or otherwise penetrating the skin. This could include actively pulling, wicking, suctioning, or otherwise drawing such emitted blood from the skin and/or form the surface of the skin into the device and/or toward some sensor, storage element, or other element(s) of the device. Further, while examples and embodiments described herein refer to accessing blood from skin, it should be understood that methods, devices, and other embodiments described herein could be employed to access other fluids from other environments of interest.

II. Example Micro-Fluid Mixing Devices and Example Operation

Example structure and operation of micro-fluid mixing devices in accordance with example embodiments are described herein by way of example in terms of micro-volume-sized devices for mixing micro-volumes of blood with micro-volumes of one or more other fluids. As described above, micro-fluid mixing of blood with one or more other micro-fluids can enable one or a variety of tests and/or analyses of blood within a physical space significantly smaller than that of typical blood-mixing and blood-testing equipment, such as may be used conventionally in a medical testing laboratory, for example. Such miniaturization of blood-mixing apparatuses can serve as technical platform for highly portable or wearable blood-testing devices, among other advances. It should be understood, however, that the principles of structure and operation illustrated herein in the context of blood-drawing and/or blood analysis are not intended to be limiting, and can be extended to other applications of metering, dispensing, filtering, and mixing of micro-fluids.

An example micro-fluid mixing device for drawing a micro-volume of blood and micro-mixing it with one or more other micro-fluids could be configured in a variety of ways. Such a device could include one or another form of a blood-drawing subsystem, which could employ a penetrating means (e.g., one or more needles) configured to be driven into the skin by injecting means (e.g., by a piston and a chemical propellant) and subsequently retracted from the skin (e.g., by a spring) such that blood can emerge from the resultant wound (e.g., puncture) in the skin. In accordance with example embodiments, the blood-drawing subsystem could be configured for drawing a micro-volume of blood, for example by using an appropriately small needle or other penetrating means.

An example blood-drawing subsystem could further include a variety of means (e.g., suction sources, seals, channels, concave depressions) configured to draw a micro-volume of blood emergent from the skin into the device, and to direct such drawn blood toward a micro-volume vessel or chamber of the example micro-fluid mixing device in preparation for, or as a stage or step of, mixing the blood with one or more other micro-fluids, as described in detail below.

In some examples, a micro-fluid mixing device could be configured to be mounted to or on skin or otherwise worn such that the device can, one or more times, draw, mix, and test a micro-volume of blood automatically. For example a controller or other element(s) of the device could operate the blood-drawing subsystem of the device to pierce the skin and draw a micro-volume of blood. The controller could further operate micro-mixing components of the device to mix the blood with one or more other micro-fluids and then carry out one or more tests on the micro-mixture. Automating operation can cause these and other associated step to be carried out while a wearer of the device sleeps, or is otherwise not actively and/or attentively engaged with the device. Alternatively, the micro-fluid mixing device could be a handheld device configured to be manually mounted to a portion of skin and operated to draw, mix, and test a micro-volume of blood. In some examples, the device could be part a wall-mounted assembly, situated on a desktop, or disposed or mounted in some other way, and mounting the device to skin could include positioning an arm or other aspect of a body proximate to the device (e.g., positioning skin of the wrist of a person proximate to a specified aspect of the device). In some examples, one or more elements (e.g., injectors, needles, seals, suction sources, sensors, blood storage elements) could be removable (e.g., disposable) from the device, e.g., while other elements of the device (e.g., controllers, user interfaces, mounts) could be reusable by replacing used removable (e.g., disposed) elements of the device.

An example of a blood-accessing micro-mixing device 100 is illustrated in FIGS. 1A and 1B. By way of example, the device 100 includes six sections, each housing, among other components, a micro-fluid mixing subsystem that includes respective micro-volume fluid chamber (µVFC), a micro-volume fluid mixing chamber (µVMC), and a respective blood-drawing subsystem configured to draw blood from adjacent dermal tissue. FIG. 1A shows an exploded perspective view of components of the first section of the device (components of other section of the device 100 are omitted for illustrative clarity). FIG. 1B is a cross-sectional view of the device 100 illustrating in detail elements of just one section of the device 100. The device 100 includes a multi-section housing 140 that is formed to include a number of µVFCs (e.g., 104), µVMCs (e.g., 106), and blood-drawing subsystem chambers (e.g., 114) of the sections as well as other features. Blood-accessing micro-mixing device 100 could be used on its own (e.g., by placing a bottom surface of the device 100 in contact with skin), could be part of another device (e.g., part of a wrist-mountable or otherwise body-mountable device), could be a removable module of another device, or could be configured or operated in some other way.

The first section includes elements disposed within a first μVFC 104 and a first blood-drawing subsystem chamber 114 formed in the housing 140. The μVFC 104 and blood-drawing subsystem chamber 114 are both shown as cylindrical shapes formed in the housing, but either could assume other shapes according to an application. The μVFC 104 houses a piston assembly including a top segment (TS) 108, a bottom segment (BS) 110, and a center shaft 112. The piston assembly is slidably accommodated in the μVFC 104 such that the TS 108 and BS 110 can slide axially (up and down with respect to the orientation of FIGS. 1A and 1B) along the shaft 112 within the μVFC 104. A sensor 142 for testing and/or analyzing one or more properties (e.g., chemical, electrochemical, etc.) of blood and/or a micro-mixture of blood with one or more other micro-fluids may be configured in the μVMC 106.

In an example embodiment, a propellant 130 is used to drive axial motion of the piston assembly from initial positions of the TS 108 and BS 110 to final positions, and a trigger 132 is used to trigger or activate release of the propellant 130 (the propellant 130 and trigger 132 are shown as a single element in FIG. 1A, but separated out in FIG. 1B). The propellant 130 may be a source of pressurized gas, such as a capsule or cartridge of pre-pressurized gas, or a container holding one or more chemical components that generate gas pressure by a chemical reaction. In one example, the trigger 132 may be a resistive element configured to ignite the propellant 130 by providing sufficient heat to the propellant 130 when current passes through the resistive element. In another example, heat from a resistive element can cause a gas-containing capsule to rupture and release pre-pressurized gas. In still another example, a resistive element can generate sufficient heat to start a chemical reaction that generates pressure. For instance, if the propellant 130 contains water, heat from the resistive element can electrolyze the water, generating expanding hydrogen and oxygen gas. Other forms of the propellant 132 and trigger 132 are possible as well.

The blood-drawing subsystem chamber 114 contains a blood-drawing subsystem 124 configured for making a small puncture in skin and drawing a micro-volume of blood that emerges from the puncture site. By way of example, blood-drawing subsystem 124 includes a piston coupled to the needle and configured to slidably move within the blood-drawing subsystem chamber 114 (e.g., along the long axis of the blood-drawing subsystem chamber 114), and a spring configured to retract the needle after the puncturing action. In an example embodiment, the piston and needle may be propelled by a propellant 126, which may be activated by a trigger 128 (the propellant 126 and trigger 128 are shown as a single element in FIG. 1A, but separated out in FIG. 1B). In example operation, the trigger 128 may cause sudden release of the propellant 126, which can then drive the needle through a seal 143 disposed on a bottom surface of the housing 140 and into skin adjacent to the seal. The trigger 128 may be a resistive element configured to ignite the propellant 126 by providing sufficient heat to the propellant 126 when current passes through the resistive element.

The top of the μVFC 104, the blood-drawing subsystem chamber 114, and the μVMC 106 are closed with an air-tight seal by a circuit board 152 or other member bonded or otherwise adhered to the housing 140. Electronics 150 (e.g., one or more controllers, logic gates, current sources, electronic switches, radio transceivers, analog-to-digital converters) disposed on the circuit board 152 could be configured to perform operations of the device 100, e.g., to apply current to the triggers 128 and/or 132 to ignite or active the propellants 126 and/or 130 at a specified point in time and/or in a specified order, to operate a sensor (e.g., sensor 142) to detect a property of blood accessed from skin and mixed with a mixer micro-fluid by the device 100, or to perform some other operations according to an application.

The cross-sectional view of FIG. 1B depicts an initial configuration of the piston assembly in the μVFC 104. As shown, the TS 108 and BS 110 are positioned such that they subdivide the interior volume of the μVFC 104 into three sub-volumes: a "top" sub-volume above the TS 108 (and sealed from above by the circuit board 152); a "middle" sub-volume between the TS 108 and BS 110; and a "bottom" sub-volume below the BS 110 (and above a "floor" of the μVFC 104). The propellant 130 and trigger 132 are affixed to the underside of the circuit board 152 within the top sub-volume such that release of the propellant 130 couples gas pressure into the top sub-volume, thereby driving the TS 108 downward. Although not necessarily shown in FIG. 1B, the middle sub-volume is filled with a mixer micro-fluid in the initial configuration of the piston assembly in the μVFC 104. The mixer micro-fluid hydraulically links motion of the TS 108 and BS 110, such that downward motion of the TS 108 causes downward motion of the BS 110, at least until the mixer micro-fluid is expelled from the middle sub-volume, as described below.

The cross-sectional view of FIG. 1B also shows a micro-fluid inlet channel 116 between the μVFC 104 and a needle channel formed in the bottom of the through the housing 140. The micro-fluid inlet channel 116 provides a fluid connection from the needle channel, where blood emerging from a puncture enters the device 100, to the μVFC 104. As such, the micro-fluid inlet channel 116 provides a fluid connection from a blood source into the μVFC 104. Also shown is a first micro-fluid outlet channel 118 that provides a first fluid connection from the μVFC 104 into the μVMC 106, and a second micro-fluid outlet channel 120 that provides a second fluid connection from the μVFC 104 into the μVMC 106. A micro-fluid outlet 122 provides a fluid outlet from the μVMC 106 to support one or another function that may require emptying the μVMC 106 after fluid mixing. For example, the outlet 122 may lead to an external sensor, as indicated in the example of FIG. 1B. Such a sensor could be used instead of or in addition to the sensor 142. In some embodiments, the micro-fluid outlet 122 may be omitted if no corresponding function for emptying the μVMC 106 exists (e.g., no external sensor).

To the extent that the cross-sectional view can be taken to represent a co-planar slice of the device 100, it may be inferred that the micro-fluid inlet channel 116 and the first and second micro-fluid outlet channels 118 and 120 are also co-planar, at least in the example embodiment illustrated in FIG. 1B. It should be appreciated that this need not be the case in other embodiments. In particular, all three micro-fluid channels might not necessarily appear together in a cross-sectional view of an embodiment in which they are not all co-planar. As such, the example shown in FIG. 1B may be considered as embodying, among other features, a configuration of micro-fluid channels that happens to make for convenient illustration in a cross-sectional view.

An opening (orifice) of each of the micro-fluid inlet channel 116 and the first and second micro-fluid outlet channels 118 and 120 in the interior wall of the μVFC 104 may be obstructed (blocked) or unobstructed (unblocked) by one or the other of the TS 108 and/or BS 110, depending on the axial positions of the two piston segments in the μVFC 104. As such, axial motion of the TS 108 and BS 110 can have the effect of opening and/or closing one or another of the micro-fluid inlet channel 116 and the first and second micro-fluid outlet channels 118 and 120. As described below, this opening and closing, together with placement, or dynamic supply, of micro-fluids into the middle and bottom sub-volumes, forms a basis for the metering, dispensing, and mixing of micro-fluids in the example device 100.

As noted above, a mixer micro-fluid fills the middle sub-volume in the initial positional configuration of the piston segments. Further, in the initial positional configuration, the BS 110 blocks the orifice of the first micro-fluid outlet channel 118, while the orifice of the micro-fluid inlet channel 116 and the orifice of the second micro-fluid outlet channel 120 are both unblocked. In addition, a respective orifice of the first and second micro-fluid outlet channels 118 and 120 in the interior wall of the μVMC 106 remains unobstructed. In particular, in the initial positional configuration, the μVMC 106, the bottom sub-volume, and the needle channel are all in hydrostatic contact by virtue of the second micro-fluid outlet channel 120 being open at both ends and the micro-fluid inlet channel 116 also being open at both ends. In further accordance with example embodiments, the μVMC 106 can be evacuated in the initial configuration to create a substantial vacuum throughout a volume that includes the bottom sub-volume, the needle channel, the second micro-fluid outlet channel 120, and the micro-fluid inlet channel 116, in addition to the μVMC 106 itself. The vacuum may be maintained by the air-tight seal of the circuit board 152 at the top and the seal 143 at the bottom. The micro-fluid outlet 122, if present, may also be sealed, at least in the initial configuration.

In the example device 100, the needle, under propulsion of the propellant 126, can be driven through the needle channel and into skin proximate the bottom of the housing 140. A piston vent (not shown) in the piston of the blood-drawing subsystem 124 and chamber vents (not shown) formed in the housing 140 may allow gases produced by the ignition of the propellant 126 to be vented out of the device such that the spring of the blood-drawing subsystem 124 can retract the needle subsequent to the ignited propellant causing the piston to drive the needle through the seal 143 and into skin. The seal 143 includes a concave depression through which the needle penetrates the seal 143 to form a hole in the seal 143 when driven downward by the piston.

Triggering the blood-drawing system 124 in the initial configuration can result in a skin puncture adjacent to the hole in the seal 143, where the initial vacuum can then draw emergent blood through the needle channel and into the bottom sub-volume by way of the micro-fluid inlet channel 116. Once the bottom sub-volume is full or nearly full, the trigger 132 may ignite or otherwise activate the propellant 130, which then drives the piston segments downward. As described in more detail below, the motion of piston segments then expels the drawn blood from the bottom sub-volume, through the second micro-fluid outlet channel 120, and into the μVMC 106. Motion of the piston segments also expels the mixer micro-fluid from the middle sub-volume, through the first micro-fluid outlet channel 118, and into the μVMC 106. Both the micro-volume of drawn blood and the mixer micro-fluid may thus be dispensed into the μVMC 106, where they can mix and be analyzed or measured by a testing strip or other measuring device or element.

The action of the trigger 132 may be under programmed control (e.g., by one or more components of the electronics 150), or may be responsive to detection of a threshold volume of drawn blood. Other techniques for trigger action may be employed as well. Additionally, the order in which the triggers 128 and 132 are invoked, together with relative physical placement of the first and second outlet channels and relative axial thicknesses of the TS 108 and BS 110, may be configured to determine an order in which the blood and the mixer micro-fluid are expelled into the μVMC 106. This too is discussed in more detail below.

FIG. 2A illustrates an enlarged cross-sectional view of an example embodiment of a blood-accessing micro-mixing device 200, and FIGS. 2B-2G illustrate example operation of the device. In particular, the example embodiment of FIGS. 2A-2G illustrate a device configuration and corresponding operation for micro-mixing blood with a mixer micro-fluid in a μVMC of the device for a use case in which, first, the blood is expelled into the μVMC, followed, next, by expulsion of the mixer micro-fluid into the μVMC.

As shown, the blood-accessing micro-mixing device 200 includes elements and components arranged in a micro-cylinder block 202 that forms a structural housing. Specifically, the micro-cylinder block 202 houses a hydraulic micro-volume cylinder chamber (HμVCC) 204, a μVMC 206, and a blood-drawing subsystem chamber 214. That is, the HμVCC 204, μVMC 206, and blood-drawing subsystem chamber 214 are micro-volume chambers (e.g., cavities) formed within the micro-cylinder block 202. The bottom of the blood-drawing subsystem chamber 214 includes a needle channel through which a needle may travel during a skin-piercing action. For the sake of brevity in the FIG. 2A, no sensor is shown in the μVMC 206 (e.g., sensor 142 in FIGS. 1A and 1B). The micro-cylinder block 202 may be a self-contained housing for a single-application micro-mixing device, or could be considered a one section of a multi-section housing, such as housing 140 in FIGS. 1A and 1B. That is, a multi-section device could be considered as including multiple (e.g., a physical array of) micro-cylinder blocks, each taking the form of the micro-cylinder block 202 and each including components as described for just one micro-cylinder block.

A micro-fluid inlet in the micro-cylinder block 202 provides a physical path for a fluid connection from the needle channel into the HμVCC 204. The micro-fluid inlet takes the form of a micro-fluid inlet channel 216 with source port 216-s at one end in the needle channel and an inlet port 216-i at the other end in an interior wall of the HμVCC 204. Both the source port 216-s and the inlet port 216-i may be considered openings (orifices) at either end of the micro-fluid inlet channel 216. They referred to herein as "ports" for convenience in the discussion, as a designation that gives structural significance to the openings.

A first micro-fluid outlet in the micro-cylinder block 202 provides a physical path for a first fluid connection from the HμVCC 204 into the μVMC 206. The first micro-fluid outlet takes the form of a first micro-fluid outlet channel 218 with a first outlet port 218-o at one end in the interior wall of the HμVCC 204 and a first inlet opening 218-i at the other end in an interior wall of the μVMC 206. Both the first outlet port 218-o and the first inlet opening 218-i may be considered openings (orifices) at either end of the first micro-fluid outlet channel 218. Again, the term "ports" is used herein for convenience in the discussion.

In a similar fashion, a second micro-fluid outlet in the micro-cylinder block 202 provides a physical path for a second fluid connection from the HμVCC 204 into the μVMC 206. The second micro-fluid outlet takes the form of a second micro-fluid outlet channel 220 with a second outlet port 220-o at one end in the interior wall of the HμVCC 204 and a second inlet opening 220-i at the other end in an interior wall of the μVMC 206. Both the second outlet port 220-o and the second inlet opening 220-i may be considered openings (orifices) at either end of the second micro-fluid outlet channel 220. Once more, the term "ports" is used herein for convenience in the discussion.

Also shown is a third micro-fluid outlet in the micro-cylinder block 202 providing physical path for a third fluid connection from the μVMC 206 to a location exterior to the μVMC 206 where testing, analysis, and or measurement could be carried out on the mixture, as mentioned above. The third micro-fluid outlet takes the form of a third micro-fluid outlet channel 222 with a third outlet port 222-o at one end in the interior wall of the μVMC 206 and a third opening (not shown). Details of a third opening are omitted in the present discussion since they don't necessarily impact on the mixing operation illustrated below. Further, some embodiments may not include a third micro-fluid outlet.

A piston assembly is placed in the HμVCC 204 such that slidable motion of both a top and bottom piston segments, TS 208 and BS 210, along an axial direction is accommodated. The piston assembly includes a central shaft 212 to help stabilize and/or guide motion of the segments within the HμVCC 204. In FIG. 2A, the piston assembly is shown in an initial configuration in which the device is ready for a blood-drawing and micro-mixing operation. In the initial configuration, the TS 208 and BS 210 divide the HμVCC 204 into a three sub-volumes: a top sub-volume 204-T, a middle sub-volume 204-M, and a bottom sub-volume 204-B. Also in the initial configuration, the first outlet port 281-o is blocked (obstructed) by the BS 210, while the first inlet port 216-i and the second outlet port 220-o are both open (unobstructed).

A blood-drawing subsystem 224 is configured in the blood-drawing subsystem chamber 214. As described above, the blood-drawing subsystem 224 includes a needle attached to a piston and a spring below the piston. The piston can move slidably in the blood-drawing subsystem chamber 214, such that the needle can be driven through the needle channel.

A propellant 226 with a trigger 228 is configured above the piston of the blood-drawing subsystem 224. Similarly, a propellant 230 with a trigger 232 is configured above the TS 208. The propellant 230 is coupled into the top sub-volume 204-T so that release by the trigger directs downward pressure on the TS 210. The propellants 226 and/or 230 could include a variety of chemicals and combinations of chemicals configured to apply gas pressure to the piston of the blood-drawing subsystem 224 or the TS 208. As such, the either propellant can also be described as being a source or pressurized gas. For example, the propellants 226 and/or 230 could include nitrocellulose, butane, azide, or some other energetic gas-producing substance or other chemical(s). In some examples, the propellant could be formed and/or modified before use, e.g., the propellant could include oxygen and hydrogen formed from water by electrolysis. Alternatively, the propellant could include a compressed gas (e.g., CO2, N2, air compressed by a pump or other means, a gas generated by the device 100 by electrolysis or some other method or means).

The triggers 228 and/or 232 resistive elements capable of igniting the propellants 226 and/or 230. Other means for igniting or activating a chemical propellant are anticipated, including but not limited to generating an electrical spark (e.g., by applying a high voltage across a spark gap or between electrodes of the device 200), illuminating the propellant (e.g., using a laser, an LED, or some other light-emitting element(s)), applying a fore and/or vibration to the propellant (e.g., using a piezoelectric elements), or changing a pressure to which the propellant is exposed. In an example embodiment, the bottom sub-volume could include an electrode connected to the trigger 232 in an open circuit that can be completed by the presence of threshold level of blood or some other micro-fluid. In such an arrangement, the propellant 230 could be ignited or activated once the threshold is achieved. The electrode could be routed through the shaft 212, for example.

Figure 2B:
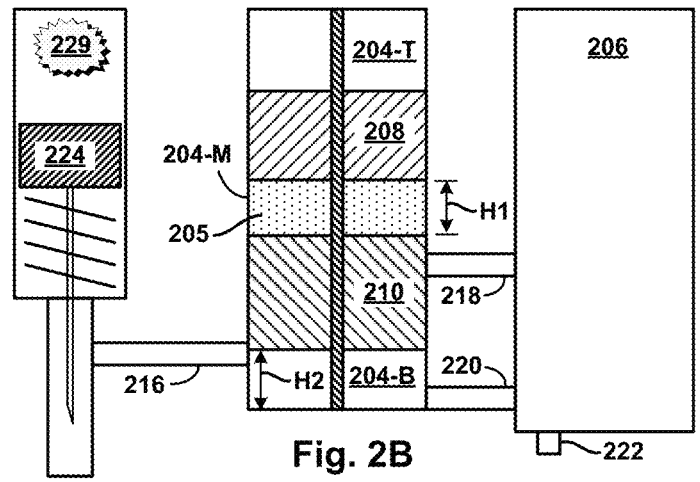
FIG. 2B is a cross-sectional view of the example device of FIG. 2A in an initial stage of operation.

Example operation of the device 200 is illustrated in FIGS. 2B-2Q which depict a sequence of operational stages of blood drawing and micro-fluid mixing. The operational stages of the sequence are not necessarily intended to represent discrete states, but rather snapshots that capture particular aspects of operation helpful in describing how the device works. For the sake of brevity in the figures, the device 200 of FIG. 2A is redrawn in a simplified, conceptual form (e.g., the micro-cylinder block 202 is assumed to be present, but not shown explicitly). In addition, item labels are omitted from most of the figures.

FIG. 2B shows the device 200 in the initial configuration. Specifically, the TS 208 and BS 210 divide the HμVCC 204 into initial top, middle, and bottom sub-volumes 204-T, 204-M, and 204-B, respectively. The micro-fluid inlet channel 216 and first and second micro-fluid outlet channels 218 and 220, respectively, are as shown in FIG. 2A. The first outlet port (not labeled) is blocked by the BS 210, and the inlet port and second outlet port (also not labeled) are unobstructed. As also shown, a mixer micro-fluid 205 fills the middle sub-volume. The mixer micro-fluid 205 is sealed between the TS and BS such that axial motion of the two is hydraulically linked as long as the seal remains. By way of example, the vertical distance between the TS 208 and the BS 210 is H1, corresponding to the initial height of the middle sub-volume 204-M. Also by way of example, the vertical distance between the BS 210 and bottom (floor) of the bottom sub-volume 204-B is H2, corresponding to the height of the bottom sub-volume 204-B.

Figure 2C:
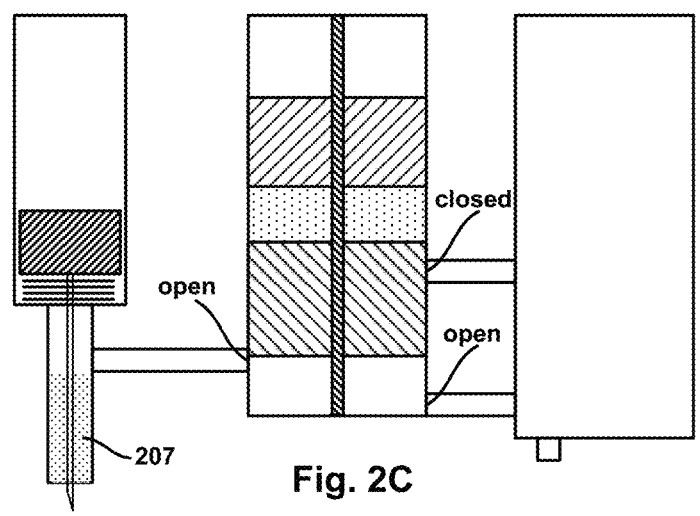
FIG. 2C is a cross-sectional view of the example device of FIG. 2A in an intermediate stage of operation.

An example blood drawing operation is initiated by activing or igniting the propellant (not shown) in the blood-drawing subsystem chamber. A cartoon "explosion" 229 represents this action, which exerts downward pressure on the blood-drawing subsystem 224. FIG. 2C next shows the piston and needle driven downward, compressing the spring, and presumably causing a small puncture in adjacent skin (not show), which results in blood 207 being drawn up into the needle chamber. At this stage, the first outlet port remains blocked, and the first inlet port and second outlet port remain unobstructed, as indicated.

Figure 2D:
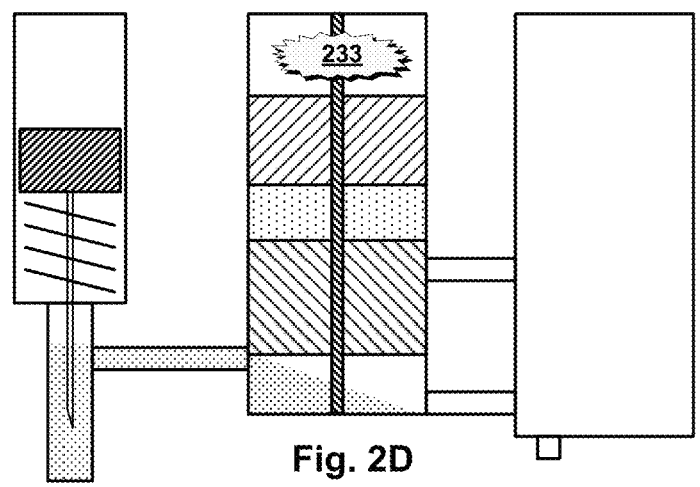
FIG. 2D is a cross-sectional view of the example device of FIG. 2A in an intermediate stage of operation.

FIG. 2D next shows the blood 207 being further drawn through the micro-fluid inlet channel and into the bottom sub-volume. Also in the stage illustrated in FIG. 2D, the propellant in the top sub-volume (not shown) of the HμVCC is activated or ignited. This too is represented by a cartoon "explosion" 233. In addition, the needle and piston have returned to their initial position under the restoring force of the spring.

Figure 2E:
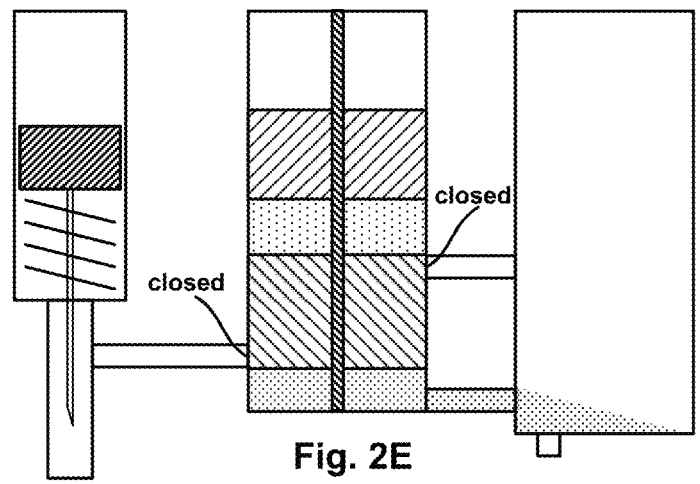
FIG. 2E is a cross-sectional view of the example device of FIG. 2A in an intermediate stage of operation.

As next illustrated in FIG. 2E, pressure exerted on the TS 208 by the propellant drives the TS downward, which in turn drives the BS downward by hydraulic pressure of the intervening mixer micro-fluid. In the particular example stage of FIG. 2E, the inlet port is now blocked by the BS, though the second outlet port remains open. The first outlet port also remains blocked by the BS. Further, the downward motion of the BS has reduced the size (height) of the bottom sub-volume, and the resulting compression acts to expel the blood from the bottom sub-volume into the μVMC by way of the second micro-fluid outlet channel, as indicated.

Figure 2F:
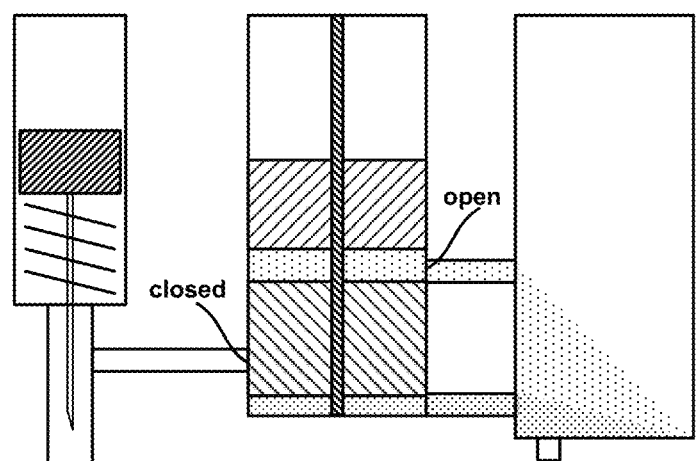
FIG. 2F is a cross-sectional view of the example device of FIG. 2A in an intermediate stage of operation.
Figure 2G:
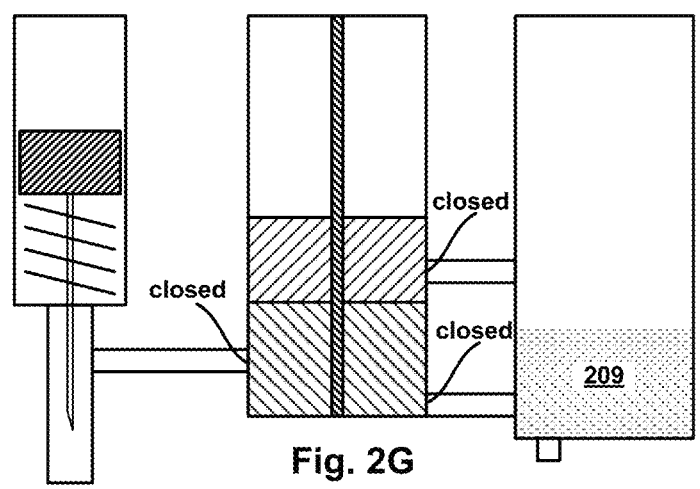
FIG. 2G is a cross-sectional view of the example device of FIG. 2A in a final stage of operation.

In the next stage, illustrated in FIG. 2F, the BS has moved far enough downward so that the first outlet port becomes unobstructed. As a result, the mixer micro-fluid in the middle sub-volume is expelled into the μVMC by way of the first micro-fluid outlet channel and under pressured of the downward motion of the TS toward the BS. This motion also reduces the size (height) of the middle sub-volume. The mixer micro-fluid and the blood also begin to mix together in the μVMC.

In the final stage illustrated in FIG. 2Q both the BS and TS have arrived at their final positions: the BS at the bottom (floor) of the HμVCC and the TS resting against the top of the BS. The middle and bottom sub-volumes have been reduced to zero, and the inlet port and first and second outlet ports are all blocked by the TS and/or BS. The blood and the mixer micro-fluid now form a mixture 209 in the μVMC. Note that in this example operation of FIGS. 2B-2Q the blood 207 is expelled into the μVMC 206 prior to expulsion of the mixer micro-fluid 205 into the μVMC 206.

An example embodiment of an alternative blood-accessing micro-mixing device 300 for a use case in which, first, the micro-mixing fluid is expelled into the μVMC, followed, next, by expulsion of the drawn blood into the μVMC is illustrated in FIGS. 3A-3G FIG. 3A illustrates an enlarged cross-sectional view of the example embodiment of a blood-accessing micro-mixing device 300, and FIGS. 2B-2G illustrate example operation of the device.

Figure 3A:
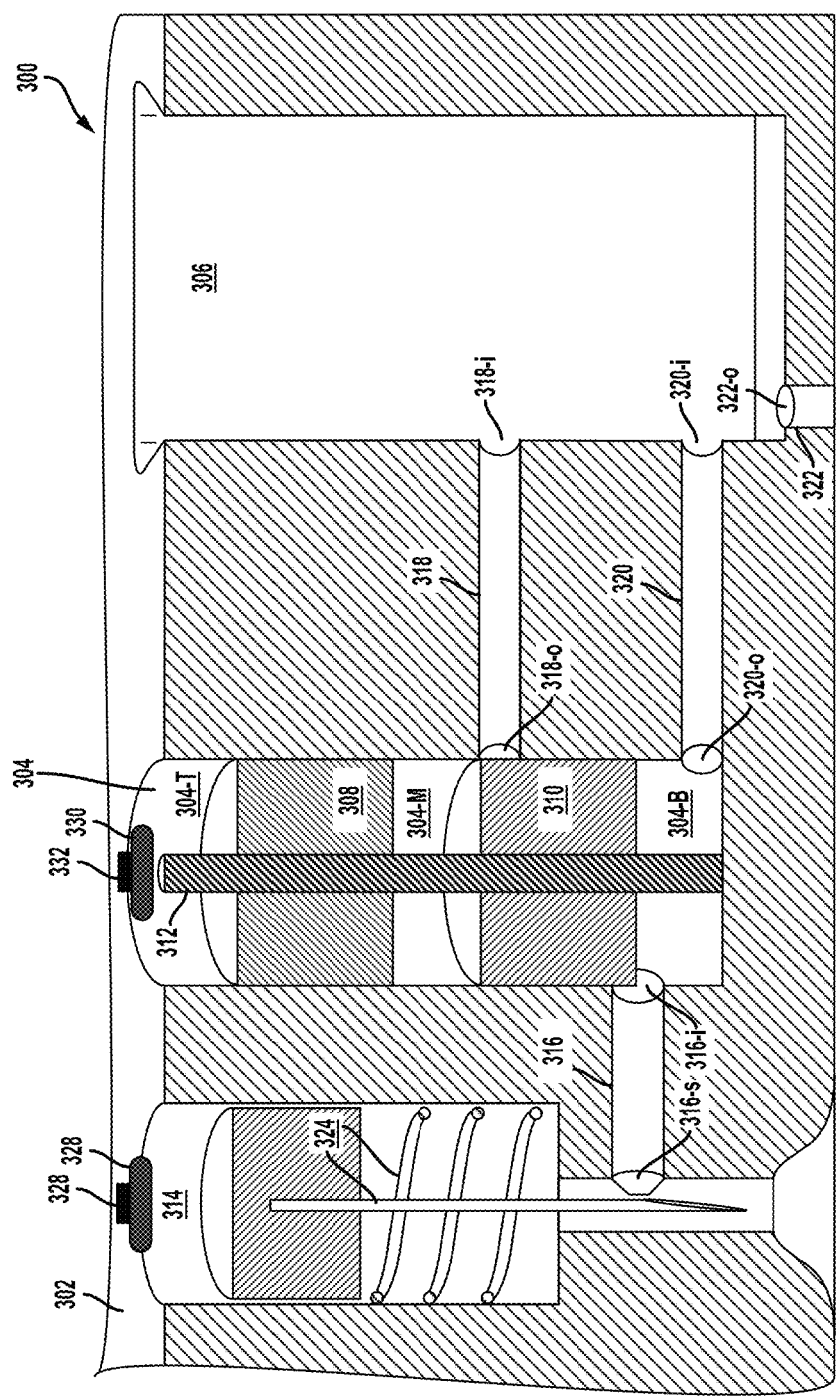
FIG. 3A is a cross-sectional view of another example device.

The example alternative blood-accessing micro-mixing device 300 depicted in FIG. 3A is largely the same as device 200 shown in FIG. 2A, with exceptions for some differences noted below. Most aspects of the discussion of the device 200 in FIG. 2A apply to the device 300 FIG. 3A, and are therefore not repeated in the discussion of the device 300. In particular, structures and features labeled "2XX" in FIG. 2A (e.g., "200," "202," . . . "232") are labeled "3XX" for like or corresponding structures and features in FIG. 3A (e.g., "300," "302," . . . "332"), and the descriptions of these structures and features of device 200 apply to the corresponding features of the device 300.

Two differences between the example device 300 and the example device 200 relevant to the order in which the two micro-fluids (blood and mixer micro-fluid) are expelled into the μVMC (206 or 306) during operation are the different axial thicknesses of the top and bottom piston segments, and the different heights of the first micro-fluid outlet channels above the bottoms (floors) of the respective HμVCCs (204 or 304). Specifically, the TS 308 of device 300 is thicker than the TS 208 of the device 200, and the BS 310 of device 300 is thicker than the BS 310 of the device 200. Additionally, the first outlet channel 318 of device 300 is higher above the bottom (floor) of the HμVCC 304 than is the first outlet channel 218 of device 200 above the bottom (floor) of the HμVCC 204. The significance of these differences may be seen by considering example operation of the device 300 illustrated in FIGS. 3B-3G.

Figure 3B:
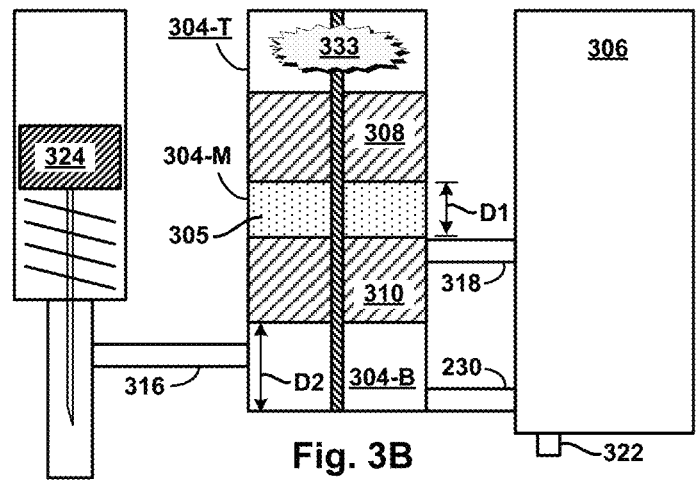
FIG. 3B is a cross-sectional view of the example device of FIG. 3A in an initial stage of operation.

FIG. 3B shows the device 300 in the initial configuration. Specifically, the TS 308 and BS 310 divide the HμVCC 304 into initial top, middle, and bottom sub-volumes 304-T, 304-M, and 304-B, respectively. The micro-fluid inlet channel 316 and first and second micro-fluid outlet channels 318 and 320, respectively, are as shown in FIG. 3A. The first outlet port (not labeled) is blocked by the BS 310, and the inlet port and second outlet port (also not labeled) are unobstructed. As also shown, a mixer micro-fluid 305 fills the middle sub-volume. The mixer micro-fluid 305 is sealed between the TS and BS such that axial motion of the two is hydraulically linked as long as the seal remains. By way of example, the vertical distance between the TS 308 and the BS 310 is D1, corresponding to the initial height of the middle sub-volume 304-M. Also by way of example, the vertical distance between the BS 310 and bottom (floor) of the bottom sub-volume 304-B is D2, corresponding to the height of the bottom sub-volume 304-B.

Operation in initial configuration begins with ignition or activation of the propellant in the top sub-volume (not shown) of the HμVCC, represented by a cartoon "explosion" 333 in FIG. 3B.

Figure 3C:
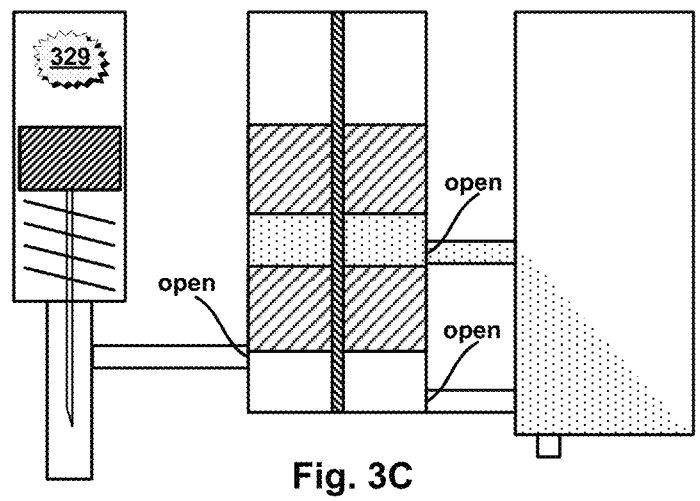
FIG. 3C is a cross-sectional view of the example device of FIG. 3A in an intermediate stage of operation.

As next illustrated in FIG. 3C, pressure exerted on the TS 308 by the propellant drives the TS downward, which in turn drives the BS downward by hydraulic pressure of the intervening mixer micro-fluid. In the particular, in the example stage of FIG. 3C, the BS has moved sufficiently downward so that the first outlet port becomes unblocked (open, as indicated). As a result, the mixer micro-fluid 305 begins to be expelled from the middle sub-volume into the μVMC 306 under pressure of the TS and by way of the first micro-fluid outlet channel, as indicated. The inlet port and second outlet port remain open. Also during this stage, the propellant in the blood-drawing subsystem chamber (not shown) is activated or ignited, as represented by a cartoon "explosion" 329.

Figure 3D:
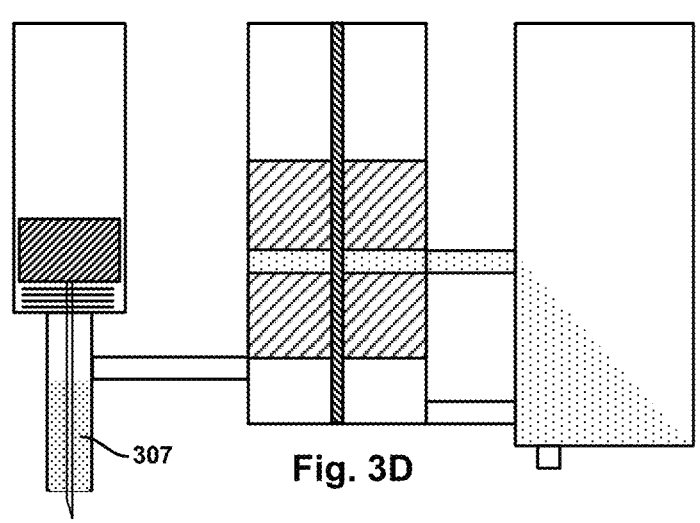
FIG. 3D is a cross-sectional view of the example device of FIG. 3A in an intermediate stage of operation.

FIG. 3D next shows the piston and needle driven downward, compressing the spring, and presumably causing a small puncture in adjacent skin (not show), which results in blood 307 being drawn up into the needle chamber. At this stage, the first outlet port remains blocked, and the first inlet port and second outlet port still remain unobstructed, and the mixer micro-fluid 305 continues to be expelled into the μVMC 306 under pressure of the TS.

Figure 3E:
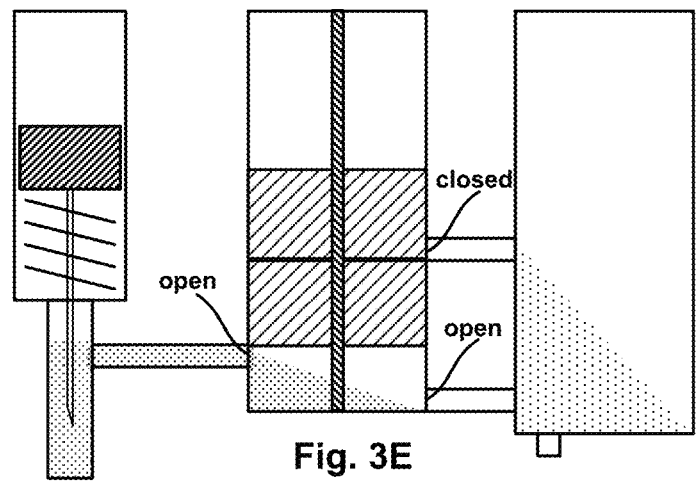
FIG. 3E is a cross-sectional view of the example device of FIG. 3A in an intermediate stage of operation.

In the next illustrative stage, shown in FIG. 3E, the blood 307 is further drawn through the micro-fluid inlet channel and into the bottom sub-volume. Also in the stage illustrated in FIG. 3E, the mixer micro-fluid 305 is evidently completely expelled from the middle sub-volume, and the middle sub-volume has been reduced to zero, with the TS now obstructing (closing) the first outlet port and resting against the top of the BS. In addition, the needle and piston have returned to their initial position under the restoring force of the spring.

Figure 3F:
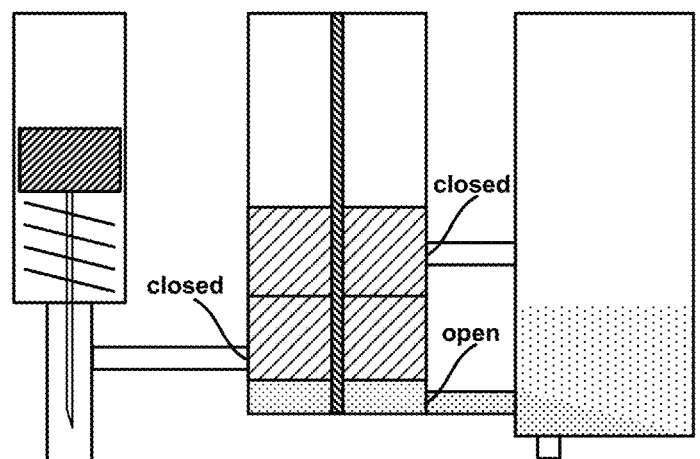
FIG. 3F is a cross-sectional view of the example device of FIG. 3A in an intermediate stage of operation.
Figure 3G:
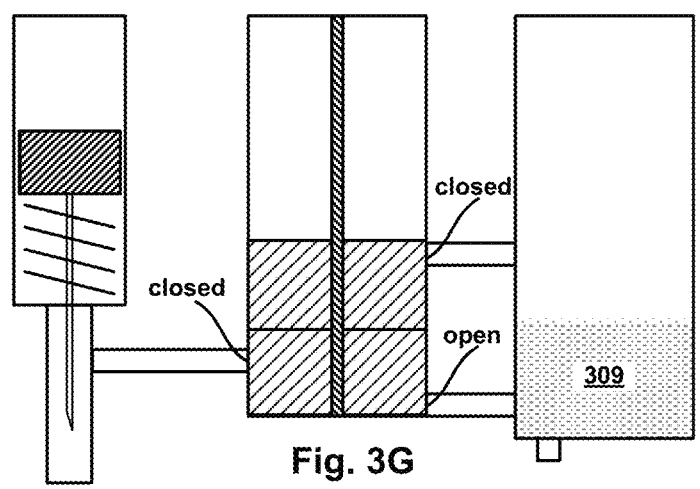
FIG. 3G is a cross-sectional view of the example device of FIG. 3A in a final stage of operation.

As next illustrated in FIG. 3F, pressure exerted on the TS 308 by the propellant drives the TS and the BS downward. In the particular example stage of FIG. 3F, the inlet port is now blocked by the BS, while the second outlet port remains open and downward motion of the BS continues to expel the blood from the bottom sub-volume into the μVMC by way of the second micro-fluid outlet channel, as indicated.

In the final stage illustrated in FIG. 3Q both the BS and TS have arrived at their final positions: the BS at the bottom (floor) of the HμVCC and the TS resting against the top of the BS. The middle and bottom sub-volumes have been reduced to zero, and the inlet port and first and second outlet ports are all blocked by the TS and/or BS. The blood and the mixer micro-fluid now form a mixture 309 in the μVMC. Note that in this example operation of FIGS. 3B-3G the mixer micro-fluid 305 is expelled into the μVMC 306 prior to expulsion of the blood 307 into the μVMC 306.

It should be understood that the particular device structures and operational stages illustrated in FIGS. 2A-2G and FIGS. 3A-3G are examples of possible architectural arrangements of the various device components (e.g., inlets, outlets, piston segment thicknesses, etc.) and possible timing sequences of micro-fluid flow that result in micro-fluid mixing according the respective specified use cases. These are not necessarily the only such architectural arrangements and consequent sequences for achieving the outcomes of the use cases. Nor do the snapshots represented in the figures correspond to all possible stages of position of the various moving parts (e.g., pistons, needles, etc.) or flow stages of the micro-fluids involved (e.g., blood and mixer micro-fluid).

It will also be appreciated that the principles of operation of devices 200 and 300, illustrated by way of example in FIGS. 2A-2G and FIGS. 3A-3G can be extended to include additional, axially arranged piston segments further subdividing a HμVCC into additional sub-volumes, as well as additional outlet channels and/or inlet channels, in order to accommodate one or more additional micro-fluids in the micro-mixing operation. For example, a third piston segment—e.g., a "middle segment" ("MS") between the TS and BS—could be used to subdivide the HμVCC into four initial sub-volumes, and the additional sub-volume could be filled with a second micro-mixing fluid. An appropriately placed additional outlet channel from the HμVCC to the μVMC could then accommodate expulsion of the second micro-fluid during one or another additional stage of operation as the additional outlet channel is blocked/unblocked by one or another of the three piston segments. Other extended configurations are possible as well.

In both of the examples of FIGS. 2A-2G and 3A-3G a micro-mixture of blood and a micro-mixing fluid is expelled from micro-volumes in a HμVCC into aμVMC. Operationally, the process is pressure driven, so description as "expelling" or "expulsion" is apt. However, from the point of view of delivery of micro-fluids into aμVMC, the process may also be considered "dispensing" of micro-fluids in the μVMC. Further, by arranging the initial middle sub-volume to have a specific size, the volume of the mixer micro-fluid dispensed may be specified. Similarly, by devising a trigger of the HμVCC to activate in response to a specific threshold of blood entering the initial bottom sub-volume, the volume of blood dispensed may similarly be specified. Accordingly, the device 200 and/or 300 may also act to meter micro-fluid dispensing. In addition, a filter may be placed in the fluid path of any one or more of the outlet channels. Doing so thereby also introduces filtering into the operation of device 200 and/or 300.

Although not explicitly depict in the example illustrations of devices 100, 200, or 300, the bottom sub-volume of the HμVCC of any one, some, or all of these devices could include a wicking material to help draw blood from the needle chamber and inlet channel into the HμVCC, and to help cause the entering blood to distribute evenly throughout the bottom sub-volume. Such a material, which could be fibrous or sponge-like, can help draw and/or distribute blood through capillary action. A uniform (or nearly so) distribution of blood in the bottom sub-volume can, in turn, cause the blood to flow more uniformly through the second outlet channel into the μVMC than it might otherwise do. It will be appreciated that the inclusion of a wicking material in the bottom sub-volume will result in a slight residual positive volume beneath the BS at the end of the micro-mixing process. That is, the initial bottom sub-volume will not be reduced completely to zero, but will retain a small space occupied by a compressed form of the wicking material.

In example devices 100, 200, and/or 300, a micro-volume of drawn blood and a mixer micro-fluid are micro-mixed in the μVMC (106, 206, or 306) of the respective example device. The micro-fluid mixture may then be applied to one or another form of blood test, measurement, and/or analysis. As mentioned above, in mixing the blood with a diluent, the mixture may be analyzed for chemical components or properties of the blood by appropriately accounting for a dilution factor. For the second example arrangement in which the mixer micro-fluid precedes the blood into the μVMC 306, the mixer micro-fluid could be a calibration fluid that is applied to a sensor to calibrate measurements made subsequently on the blood. Other possible arrangements are possible as well.

More particularly, the micro-fluid mixture dispensed into the μVMC 206 and/or 306 may be tested, measured, and/or analyzed for one or more chemical and/or electrochemical properties by a sensor, such as sensor 142, returning again to FIGS. 1A and 1B. In accordance with example embodiments, the sensor 142 could be configured to detect a variety of properties of blood drawn into the device 100, 200 or, 300, and micro-mixed with one or more mixer micro-fluids. For example, the sensor 142 could be configured to detect the presence, concentration, or other properties of an analyte (e.g., glucose, small molecules, cells, cell counts, hormones, cholesterol, testosterone, thyroid hormones, vitamins, minerals, electrolytes, cortisol, creatinine, luteinizing hormone, follicle stimulating hormone) in the blood. In some examples, the sensor 142 could be configured to detect a clotting rate, viscosity, osmolarity, or other property of the blood. The sensor 142 could be configured to detect the property of the blood through direct contact between the blood and one or more elements of the sensor 142. For example, the sensor 142 could be an electrochemical sensor configured to amperometrically, potentiometrically, or otherwise electrochemically detect one or more properties of the blood when the blood comes into contact with one or more electrodes of the electrochemical sensor (e.g., when the blood comes into contact with a working electrode of the sensor 142 that is selectively sensitive to an analyte of interest in the blood and further comes into contact with a reference electrode of the sensor 142). In another example, the sensor 142 could be configured to detect a property of the blood when the blood comes into contact with an analyte-sensitive chemical (e.g., a fluorophore, a chromophore) that has one or more optical properties (e.g., a color, a fluorescence intensity, a fluorescence lifetime) that are related to the analyte in the blood, and the sensor 140 could detect the analyte in the blood by optically interrogating (e.g., illuminating and/or detecting light emitted from) the analyte-sensitive chemical. Additionally or alternatively, the sensor 142 could be configured to detect one or more properties of the blood without being in direct contact with the blood, e.g., by detecting a color of the blood, a property of motion of the blood, or some other property.

A blood-accessing and micro-mixing device or system as described herein (e.g., 100, 200, 300) could include multiple sensors, blood-storage elements, needles, injectors, seals, and/or other elements. As illustrated in FIG. 1A, device 100 includes six sections, each section corresponding to a micro-cylinder block 202 or 320 and the various components thereof as described above, for example. Each section is configured to drive its respective needle into skin, to subsequently retract the needle from the skin, and the receive blood emitted from the skin in response to being penetrated by the needle, and micro-mix the blood with a micro-mixing fluid for testing and possible storage. Each section could include one or more sensors, one or more blood storage elements, and/or additional components configured to receive, transmit, measure, modify, or otherwise interact with blood received from the skin. The sections of a device could be similarly configured (e.g., could include similar sensors, be configured to draw similar amounts of blood from skin in a similar manner) or could be differently configured (e.g., different sensors, differently configured injectors, differently configured needles). The sections of a device could be operated to access blood from skin at respective different points in time, e.g., at a number of points in time while a wearer of the device is asleep, at a number of points in time during a week, in response to a command received from a user and/or from a remote system in communication (e.g., wireless communication via Bluetooth, ZigBee, WiFi, or some other wireless communications protocol), in response to a detected command (e.g., a button press) and/or behavior (e.g., performance of an exerting athletic activity, detected using, e.g., an accelerometer of the device 100) of a wearer, based on a detected physiological state of the wearer (e.g., a heart rate or blood pressure detected by sensor(s) of the device 100), or according to some other scheme.

Further, a device could include more or fewer sections (e.g., micro-cylinder blocks), organized similarly or differently (e.g., in a row, rather than circularly as illustrated) than those embodiments illustrated herein. For example, a blood-accessing and micro-mixing device could include a single section. In examples having just a single micro-cylinder block and components thereof, the blood-accessing and micro-mixing device could be configured for a single use. In some examples, such a single and/or limited-use (e.g., six uses, as illustrated in FIG. 1A) could be configured to be a removable and/or replaceable element of some other device. For example, the blood-accessing and micro-mixing device 100 could be configured to be removably mounted on or within a body-mountable device (e.g., a wrist-mountable device) that includes a controller, a user interface, a battery, a communications interface, or some other elements. Such a body-mountable device could be configured to operate the limited-use blood-accessing and micro-mixing device to access a number of samples of blood from skin (e.g., at respective specified points in time). Once the body-mountable device has operated all of the limited-use sections of the blood-accessing device, the blood-accessing device could be removed from the body-mountable device and replaced. In some examples, the removed blood-accessing device could be configured to store blood, and blood stored in the removed blood-accessing device could be presented to a sensing device for analysis (e.g., the removed blood-accessing device could be sent via post to a sensing device at a laboratory that is remote from a user of the body-mountable device).

Note that the configurations and operations of devices as described herein are meant as non-limiting examples of operation of devices configured to puncture skin and to receive and micro-mix blood emitted from the skin in response to being punctured. Such devices could include a variety of means for penetrating or piercing skin, for driving such penetrating means into skin, for subsequently retracting such penetrating means from the skin, for drawing, wicking, suctioning, or otherwise receiving blood responsively emitted from the skin, for storing the received blood, for sensing one or more properties of the received blood, for moving, directing, preserving, or otherwise interacting with the received blood, or for performing some additional or alternative operations of functions according to an application.

While example embodiments described so far involve micro-mixing devices for blood-drawing and/or blood-testing applications, the operational principles in regard to pressure-driven dispensing of one or more micro-fluids from respective, compressible micro-volume chambers or vessels into a common micro-volume mixing chamber or vessel, and specified relative timing of the dispensing actions, can be used for other micro-fluid applications as well. More particularly, an alternative embodiment can involve a device for micro-mixing a "target" micro-fluid with one or more mixer micro-fluids. In an example alternative embodiment based in part on a device similar to either device 200 or 300, for instance, a blood-drawing sub-system (e.g., 224 or 324) could be replaced with a source of a target micro-fluid. The source could be a pre-filled micro-volume vessel, or a dermal-piercing sub-system for accessing biologic fluids other than blood, for example. In either case, the source of the target micro-fluid could be trigger-activated and have a fluid connection, such as a micro-fluid inlet channel with an inlet port, into a HµVCC of the device. Except for the replacing a blood-drawing sub-system with a source of the target micro-fluid, construction and operation of such an alternative device could be largely similar to that described above for either of devices 200 or 300. Devised in this way, the alternative embodiment can be considered to encompass a blood-accessing and micro-mixing device, such as devices 200 and 300, as a particular form of embodiment.

A further alternative embodiment, still based on the operational principles of pressure-driven dispensing of one or more micro-fluids from respective, compressible micro-volume vessels into a common micro-volume mixing chamber or vessel, and specified relative timing of the dispensing actions, involves an example device having two or more micro-fluid chambers each with at least one deformable wall or deformable surface boundary. An example of such a micro-fluid chamber could be a micro-volume pouch. In one example, one micro-volume pouch could be filled with a target micro-fluid, while each of one or more additional micro-fluid pouches could be filled with respective mixer micro-fluids. Each pouch could have an initially sealed outlet port connected to a respective micro-fluid outlet channel leading to a common micro-fluid mixing chamber. The pouches could be arranged in a rigid chamber such that delivery of pressurized gas (e.g., propellant) into the rigid chamber can squeeze (compress) the pouches, causing the respective seals to rupture, and expelling the contain micro-fluids through the outlet ports and into the micro-fluid mixing chamber via the outlet channels. In a further aspect, one of the pouches could have an inlet port for receiving the target micro-fluid from a source of the target micro-fluid. Triggered operation, similar to that described above could be used to first deliver the target micro-fluid to the target micro-fluid pouch, and then drive subsequent compression of the pouches and resultant micro-fluid mixing. Relative timing or ordering of the expulsion of micro-fluids from the pouches could be specified by an ordered stacking of the pouches within the rigid chamber for example. Other techniques could be devised as well.

A further form of this embodiment could involve micro-fluid chambers having one flexible wall or surface that is deformable under pressure. Applying external pressure to such a micro-fluid chamber could then expel a contained micro-fluid. Note to the extent that a piston segment can be considered a deformable wall or boundary surface of micro-volume chamber, the example embodiments involving piston segments described above may be considered particular forms of a more generalized embodiment involving compressible micro-volumes.

III. Example Wearable Devices

Wearable blood-accessing and micro-mixing devices as described herein by way of example can be configured to be mounted to an external body surface of a wearer and to enable a variety of applications and functions including accessing blood of the wearer (e.g., drawing, extracting, or otherwise receiving blood), storing such accessed blood, detecting one or more properties of such accessed blood, detecting some other properties of the body of the wearer (e.g., a pulse rate), or performing some other functions. Such wearable devices could enable a variety of applications, including measuring homological properties or other physiological information about a wearer, indicating such measured information or other information to the wearer (e.g., using a vibrator, a screen, a beeper), recording such information, indicating such information to a remote system (e.g., a server in a physician's office), or other functions.

Figure 4A:
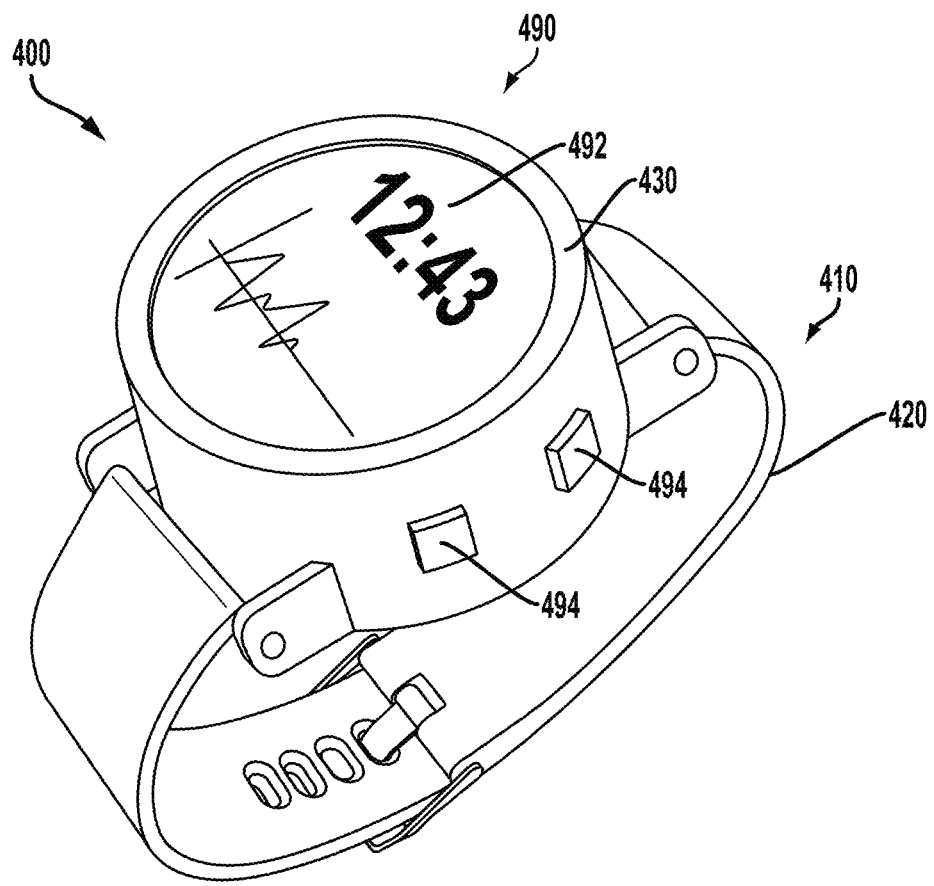
FIG. 4A is a perspective top view of an example body-mountable device.
Figure 4B:
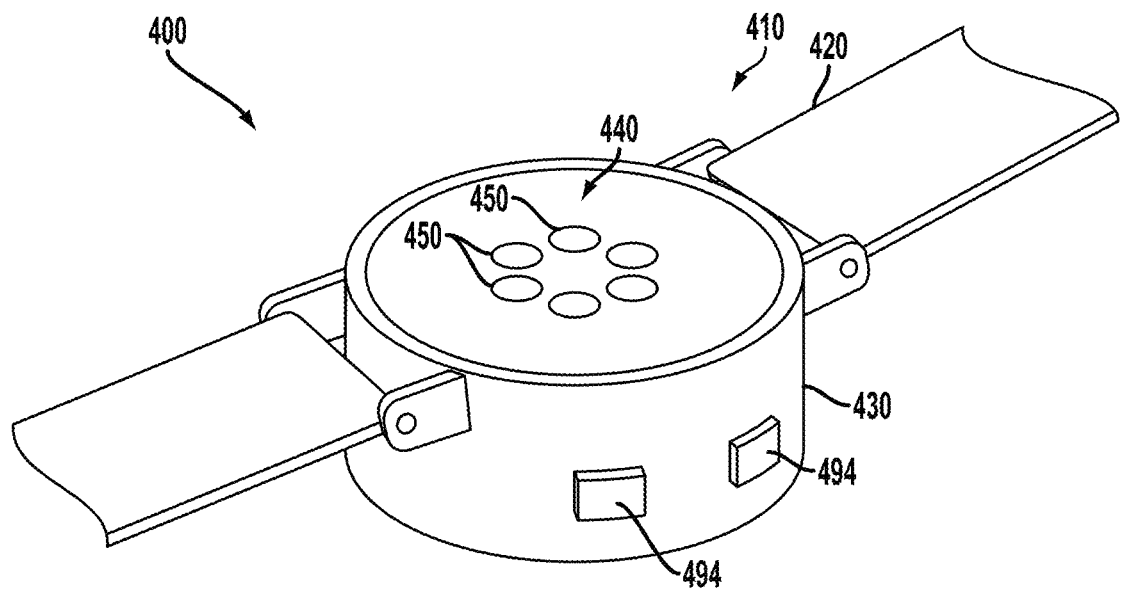
FIG. 4B is a perspective bottom view of the example body-mountable device shown in FIG. 4A.

In some examples, a wearable device 400 (illustrated in FIG. 4) is provided as a wrist-mounted device, as shown in FIGS. 4A and 4B. The wrist-mounted device 400 may be mounted to the wrist of a living subject with a wristband or cuff, similar to a watch or bracelet. The wearable device 400 can be configured to access and micro-mix blood of a wearer and to store, detect a property of, or otherwise interact with such micro-mixed blood mixture. The term "wearable device," as used in this disclosure, refers to any device that is capable of being worn at, on or in proximity to a body surface, such as a wrist, ankle, waist, chest, or other body part. In order to access blood from within and/or beneath skin of the body, the wearable device may be positioned on a portion of the body where subsurface vasculature or other targets or elements of the body of the wearer are easily accessed (e.g., punctured), the qualification of which will depend on the type of system used. A mount 410, such as a belt, wristband, ankle band, etc. can be provided to mount the device at, on or in proximity to the body surface. The mount 410 may prevent the wearable device from moving relative to the body to allow for blood to be drawn from a puncture produced in the skin by the device 400 (e.g., by a driven and subsequently retracted needle of the device) or according to some other application or consideration. In one example, shown in FIGS. 4A and 4B, the mount 410 may take the form of a strap or band 420 that can be worn around the wrist (or some other part) of the body. Further, the mount 410 may be an adhesive substrate for adhering the blood-accessing and micro-mixing device 400 to the body of a wearer.

A housing 430 is disposed on the mount 410 such that it can be positioned on the body. A contact surface 440 of the housing 430 is intended to be mounted facing to the external body surface. The housing 430 may include sensors for detecting one or more physiological properties of the wearer (e.g., a pulse, a blood oxygenation, a galvanic skin response). The contact surface 440 additionally includes a number of concave depressions 450. Each concave depression 450 corresponds to a blood-accessing section of the device 400 that can be operated to drive a needle, through the concave depression (e.g., through a seal of the device and/or through a channel of the device configured to allow the passage of the needle), into skin of a wearer and subsequently to retract the needle from the skin. Further, each section is configured to receive blood responsively emitted from the skin (e.g., by wicking, capillary action, application of suction, or some other means) and to micro-mix the blood for testing/analysis and/or storage.

The housing 430 could be configured to be water-resistant and/or water-proof. That is, the housing 430 could be configured to include sealants, adhesives, gaskets, welds, transparent windows, apertures, press-fitted seams, and/or other joints such that the housing 430 is resistant to water entering an internal volume or volumes of the housing 430 when the housing 430 is exposed to water. The housing 430 could further be water-proof, i.e., resistant to water entering an internal volume or volumes of the housing 430 when the housing 430 is submerged in water. For example, the housing 430 could be water-proof to a depth of 1 meter, i.e., configured to resist water entering an internal volume or volumes of the housing 430 when the housing 430 is submerged to a depth of 1 meter.

The wearable device 400 may also include a user interface 490 via which the wearer of the device may receive one or more recommendations or alerts generated either from a remote server or other remote computing device, or from a processor within the device. The alerts could be any indication that can be noticed by the person wearing the wearable device 400. For example, the alert could include a visual component (e.g., textual or graphical information on a display), an auditory component (e.g., an alarm sound), and/or tactile component (e.g., a vibration). Further, the user interface 490 may include a display 492 where a visual indication of the alert or recommendation may be displayed. The display 492 may further be configured to provide an indication of a measured hemodynamic property of blood accessed and micro-mixed from the body of the wearer using the device (e.g., to provide an indication of a blood glucose level of the wearer's blood).

Further, the user interface 490 may include one or more buttons 494 for accepting inputs from the wearer. For example, the buttons 494 may be configured to change the text or other information visible on the display 492. The buttons 494 may be configured to accept inputs for controlling aspects of the data collection system, such as initiating a measurement period (e.g., causing the device 400 to access blood of the wearer by driving a needle into skin or according to some other method), inputs indicating the wearer's current health state (i.e., normal, migraine, shortness of breath, heart attack, fever, "flu-like" symptoms, food poisoning, etc.), or inputs indicating the wearer's activities (e.g., eating a meal, taking a medication).

Note that example devices herein are configured to be mounted to a wrist of a wearer. However, the embodiments described herein could be applied to other body parts (e.g., an ankle, a thigh, a chest, an abdomen, a forehead, a thigh, a finger), or to detect hematological properties or other physiological properties in other environments. For example, embodiments described herein could be applied to detect one or more properties in a target environment (e.g., a natural environment, an environment of an industrial, pharmaceutical, or water treatment process).

Figure 5A:
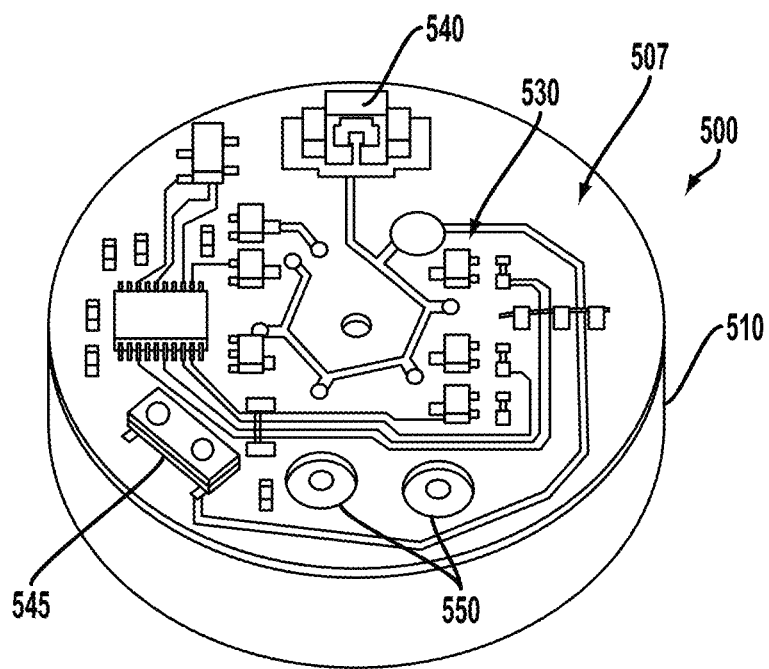
FIG. 5A is a perspective top view of an example body-mountable device.
Figure 5B:
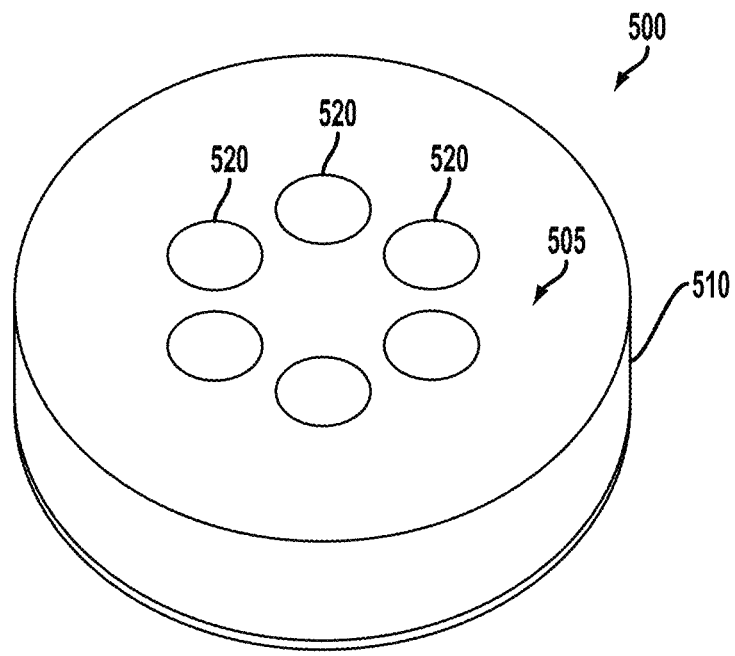
FIG. 5B is a perspective bottom view of the example body-mountable device shown in FIG. 5A.

Blood-accessing sections of the device 400 could be single-use; for example, an injector of one or more sections could ignite a limited supply of a propellant and/or wherein suction is provided for/in a section by a single micro-mixing volume. In such examples, such single and/or limited-use blood-accessing sections could be configured to be a removable and/or replaceable element of the wearable device 400. For example, FIGS. 5A and 5B show a blood-accessing and micro-mixing device 500 that could be configured to be removably mounted on or within the wearable device 400. The blood-accessing device 500 includes a housing 510 that can be positioned on skin of a body when the blood-accessing device 500 is mounted on or within the wearable device 500 and the wearable device 500 is mounted to the body. A contact surface 505 of the housing 510 is intended to be mounted facing to the external body surface. The contact surface 505 includes a number of concave depressions 520. Each concave depression 520 corresponds to a blood-accessing section of the blood-accessing and micro-mixing device 500 that can be operated (e.g., when mounted on or within the wearable device 500) to drive a needle, through the concave depression (e.g., through a seal of the device and/or through a channel of the device configured to allow the passage of the needle), into skin of a wearer and subsequently to retract the needle from the skin. Further, each section is configured to receive blood responsively emitted from the skin (e.g., by wicking, capillary action, application of suction, or some other means) and to store, detect a property of, or otherwise interact with the received blood.

The wearable device 400 could be configured to operate the blood-accessing and micro-mixing device 500 to access a number of samples of blood from skin (e.g., at respective specified points in time). Once the body-mountable device has operated all of the sections of the blood-accessing device 500, the blood-accessing and micro-mixing device 500 could be removed from the wearable device 400 and replaced. In some examples, this could include operating one or more injectors, suction sources, and/or other components of the blood-accessing and micro-mixing device 500 (e.g., via electrical connector 540, optical receiver/transmitter 545, and/or electronics 530). Additionally or alternatively, the wearable device 500 could operate the blood-accessing device 500 using other means, e.g., by igniting propellant of the blood-accessing device 500 by heating the propellant using a laser of the wearable device 500.

In some examples, the removed blood-accessing and micro-mixing device 400 could be configured to store a micro-mixture of blood and one or more mixer micro-fluids, and the mixture stored in the removed blood-accessing and micro-mixing device 500 could be presented to a sensing device for analysis (e.g., the removed blood-accessing and micro-mixing device 500 could be sent via post to a sensing device at a laboratory that is remote from a user of the body-mountable device 400). For example, samples of blood micro-mixture stored within the blood-accessing and micro-mixing device 500 could be accessed via ports 550 of the blood-accessing and micro-mixing device 500.

Additionally or alternatively, the wearable device 400 could be configured to detect one or more properties of the blood accessed and micro-mixed using the blood-accessing and micro-mixing device 500. In some examples, the blood-accessing and micro-mixing device 500 could include one or more sensors configured to detect one or more properties of a blood micro-mixture. The wearable device 400 could operate the sensors of the blood-accessing and micro-mixing device 500 (e.g., via electrical connector 540, optical receiver/transmitter 545, and/or electronics 530). Additionally or alternatively, the wearable device 400 could be configured to illuminate and/or receive light emitted from the blood-accessing device 400 (e.g., to illuminate and/or receive light emitted from an analyte-sensitive chemical that has one or more optical properties that is related to the analyte in the blood), via a window, optical fiber, or other optically transparent element(s) of the blood-accessing and micro-mixing device 500) to detect one or more properties of the blood drawn, wicked, micro-mixed, or otherwise received from skin by the blood-accessing and micro-mixing device 500.

Wearable blood-accessing devices and other embodiments as described herein can include a variety of components configured in a variety of ways. Devices described herein could include electronics including a variety of different components configured in a variety of ways to enable applications of the wearable device. The electronics could include controllers, amplifiers, switches, display drivers, touch sensors, wireless communications chipsets (e.g., Bluetooth radios or other radio transceivers and associated baseband circuitry to enable wireless communications between the wearable device and some other system(s)), or other components. The electronics could include a controller configured to operate one or more sensors, injectors, suction sources, and/or components of a blood-accessing and micro-mixing device to detect one or more hematological or other properties of a body and/or to access and store or otherwise interact with blood from within and/or beneath skin of the body. The controller could include a processor configured to execute computer-readable instructions (e.g., program instructions stored in data storage of the wearable device) to enable applications of the wearable device. The electronics can include additional or alternative components according to an application of the wearable device.

Wearable or otherwise-configured blood-accessing and micro-mixing devices as described herein could include one or more user interfaces. A user interface could include a display configured to present an image to a wearer and to detect one or more finger presses of a wearer on the interface. The controller or some other component(s) of the electronics could operate the user interface to provide information to a wearer or other user of the device and to enable the wearer or other user to affect the operation of the wearable device, to determine some property of the wearable device and/or of the wearer of the wearable device (e.g., a hematological property of blood and/or a health state of a wearer of the wearable device), or to provide some other functionality or application to the wearer and/or user. As one example, the wearer could press an indicated region of the user interface to indicate that the wearable device should begin logging detected medical information about the wearer. Other indicated information, changes in operation of the wearable device, or other functions and applications of the user interface are anticipated.

Note that the embodiments illustrated in the figures are illustrative examples and not meant to be limiting. Alternative embodiments, including more or fewer components in alternative configurations are anticipated. A wearable, handheld, body-mountable, desktop, or otherwise configured device could include multiple housings or other such assemblies each containing some set of components to enable applications of such a device. A blood-accessing and micro-mixing device as described herein could be configured to perform a variety of functions and to enable a variety of applications. Blood-accessing and micro-mixing devices could be configured to operate in concert with other devices or systems; for example, blood-accessing devices could include a wireless communication interface configured to transmit data indicative of one or more properties of the blood of a wearer of the wearable device. Other embodiments, operations, configurations, and applications of a blood-accessing device as described herein are anticipated.

FIG. 6 is a simplified schematic of a system including one or more wearable blood-accessing devices 600. The one or more wearable devices 600 may be configured to transmit data via a communication interface 610 over one or more communication networks 620 to a remote server 630. In one embodiment, the communication interface 610 includes a wireless transceiver for sending and receiving communications to and from the server 630. In further embodiments, the communication interface 610 may include any means for the transfer of data, including both wired and wireless communications. For example, the communication interface may include a universal serial bus (USB) interface or a secure digital (SD) card interface. Communication networks 620 may be any one of may be one of: a plain old telephone service (POTS) network, a cellular network, a fiber network and a data network. The server 630 may include any type of remote computing device or remote cloud computing network. Further, communication network 620 may include one or more intermediaries, including, for example wherein the wearable device 600 transmits data to a mobile phone or other personal computing device, which in turn transmits the data to the server 630.

In some examples, multiple wearable devices 600 could be configured to access and micro-mix blood from and/or detect multiple hematological or other properties of a single wearer. For example, the single wearer could wear or otherwise operate two or more wearable devices 600 to measure respective hematological or other physiological properties from respective two or more portions of the body of the wearer (e.g., respective portions of subsurface vasculature of the wearer) and/or during different periods of time (e.g., the wearable devices 600 used by the wearer could be limited-use devices, e.g., each including a discrete number of single-use blood-accessing sections).

In addition to receiving communications from the wearable device 600, such as collected hematological properties or other collected physiological properties and data regarding health state as input by the user and/or one or more properties of a wearer detected using a sensor disposed in the wearable device 600, the server may also be configured to gather and/or receive either from the wearable device 600 or from some other source, information regarding a wearer's overall medical history, environmental factors and geographical data. For example, a user account may be established on the server for every wearer that contains the wearer's medical history. Moreover, in some examples, the server 630 may be configured to regularly receive information from sources of environmental data, such as viral illness or food poisoning outbreak data from the Centers for Disease Control (CDC) and weather, pollution and allergen data from the National Weather Service. Further, the server may be configured to receive data regarding a wearer's health state from a hospital or physician. Such information may be used in the server's decision-making process, such as recognizing correlations and in generating clinical protocols.

Additionally, the server may be configured to gather and/or receive the date, time of day and geographical location of each wearer of the device during each measurement period. Such information may be used to detect and monitor spatial and temporal spreading of diseases. As such, the wearable device may be configured to determine and/or provide an indication of its own location. For example, a wearable device may include a GPS system so that it can include GPS location information (e.g., GPS coordinates) in a communication to the server. As another example, a wearable device may use a technique that involves triangulation (e.g., between base stations in a cellular network) to determine its location. Other location-determination techniques are also possible.

The server may also be configured to make determinations regarding the efficacy of a drug or other treatment based on information regarding the drugs or other treatments received by a wearer of the device and, at least in part, the hematological property data and the indicated health state of the user. From this information, the server may be configured to derive an indication of the effectiveness of the drug or treatment. For example, if a drug is intended to control a blood sugar of a wearer and the wearer of the device does not indicate that they are experiencing nausea, lightheadedness, or other sequelae after beginning a course of treatment with the drug, the server may be configured to derive an indication that the drug is effective for that wearer.

Further, some embodiments of the system may include privacy controls which may be automatically implemented or controlled by the wearer of the device. For example, where a wearer's collected hematological property data and health state data are uploaded to a cloud computing network for trend analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, wearers of a device may be provided with an opportunity to control whether or how the device collects information about the wearer (e.g., information about a user's medical history, social actions or activities, profession, a user's preferences, or a user's current location), or to control how such information may be used. Thus, the wearer may have control over how information is collected about him or her and used by a clinician or physician or other user of the data. For example, a wearer may elect that data, such as health state and hematological properties, collected from his or her device may only be used for generating an individual baseline and recommendations in response to collection and comparison of his or her own data and may not be used in generating a population baseline or for use in population correlation studies.

IV. Example Electronics

Figure 7:
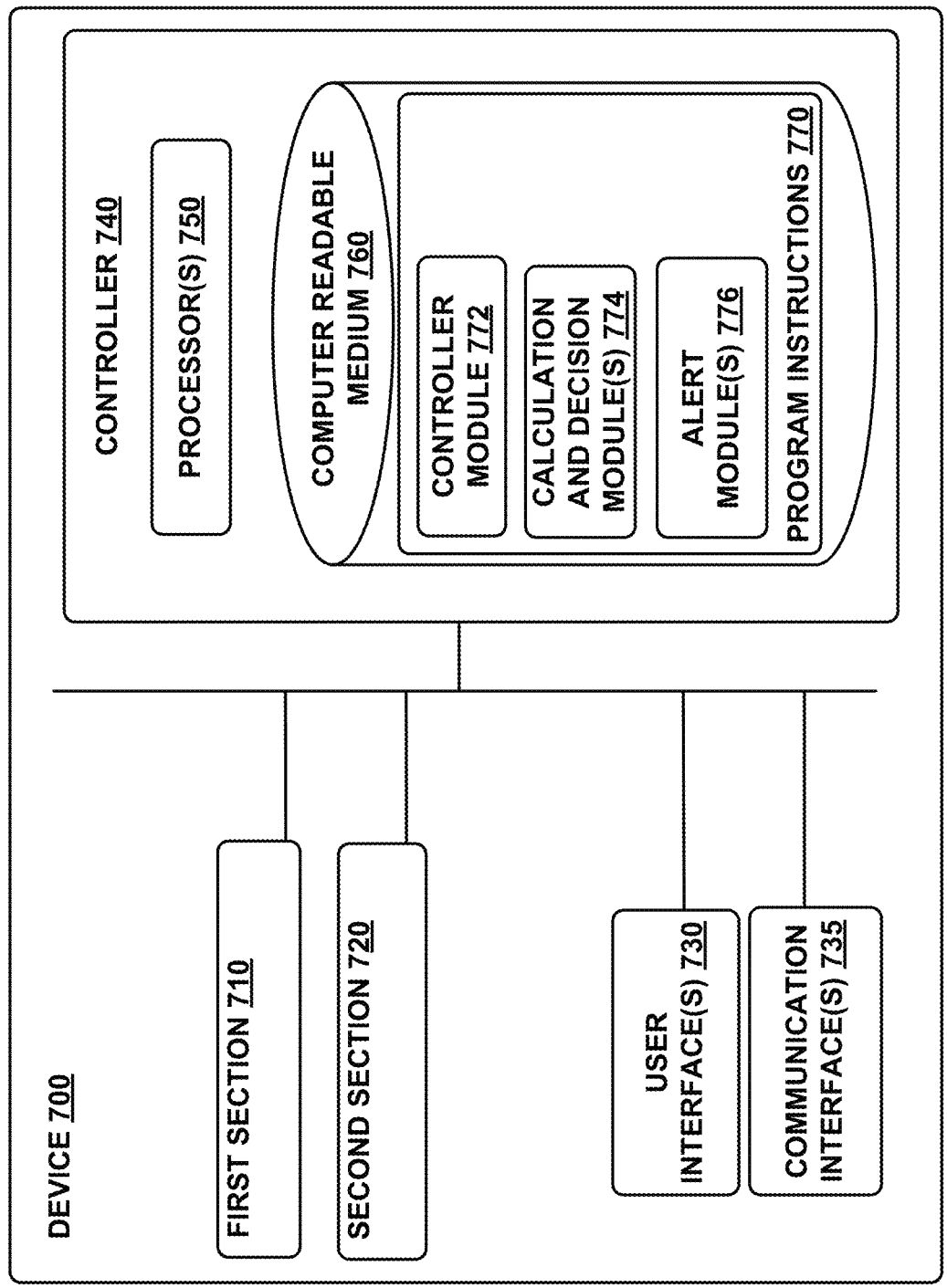
FIG. 7 is a functional block diagram of an example device.

FIG. 7 is a simplified block diagram illustrating the components of a device 700, according to an example embodiment. Device 700 may take the form of or be similar to one of the example blood-accessing and micro-mixing devices 100, 200, or 300 shown in FIG. 1A-1B, 2A-G or 3A-3G However, device 700 may also take other forms, such as an ankle, waist, or chest-mounted device. Device 700 could also take the form of a device that is not configured to be mounted to a body. For example, device 700 could take the form of a handheld device configured to be maintained in proximity to skin by a user or operator of the device 700 or by a frame or other supporting structure. Device 700 also could take other forms.

In particular, FIG. 7 shows an example of a device 700 having first 710 and second 720 blood-accessing and micro-mixing sections, a user interface 730, communication interface 735 for transmitting data to a remote system, and a controller 740. The components of the device 700 may be disposed on a mount or on some other structure for mounting the device to enable stable collection and micro-mixing of blood emitted from skin in response to penetration of the skin by one or more needles of the device 700, for example, mounting to an external body surface where one or more portions of subsurface vasculature or other anatomical elements are readily accessible.

Controller 740 may be provided as a computing device that includes one or more processors 750. The one or more processors 750 can be configured to execute computer-readable program instructions 770 that are stored in the computer readable data storage 760 and that are executable to provide the functionality of a device 700 described herein.

The computer readable medium 760 may include or take the form of one or more non-transitory, computer-readable storage media that can be read or accessed by at least one processor 750. The one or more computer-readable storage media can include volatile and/or non-volatile storage components, such as optical, magnetic, organic or other memory or disc storage, which can be integrated in whole or in part with at least one of the one or more processors 750. In some embodiments, the computer readable medium 760 can be implemented using a single physical device (e.g., one optical, magnetic, organic or other memory or disc storage unit), while in other embodiments, the computer readable medium 760 can be implemented using two or more physical devices.

First 710 and second 720 blood-accessing sections could include any components configured to drive a needle into skin, to subsequently retract the needle from the skin, to receive blood from the resulting puncture in the skin (e.g., by applying suction to the skin), and micro-mix the blood with one or more micro-mixing fluids, and to perform other functions as described elsewhere herein. Blood-accessing sections could include motors, piezoelectric transducers, solenoids, actuated valves, resistive heaters or other propellant-igniting components, or other components of an injector configured to drive a needle into skin and/or to subsequently retract such a needle. Blood-accessing and micro-mixing sections 710, 720 could include blood-storage elements as described elsewhere herein to store blood for, e.g., later analysis. Blood-accessing and micro-mixing sections 710, 720 could include sensors configured to detect a variety of properties of blood drawn, wicked, suctioned, received, or otherwise accessed by the blood-accessing micro-mixing sections 710, 720. The device 700 could include additional (or fewer) blood-accessing and micro-mixing sections. The blood-accessing and micro-mixing sections 710, 720 could be similarly or differently configured. The blood-accessing and micro-mixing sections 710, 720 could be part of a removable and/or replaceable portion of the device 700. The device 700 may include further sensors (not shown), e.g., heart rate sensors, galvanic skin response sensors, pulse oximeters, or other sensors configured to detect one or more properties of the body of a wearer and/or of the environment of the device 700.

The program instructions 770 stored on the computer readable medium 760 may include instructions to perform any of the methods described herein. For instance, in the illustrated embodiment, program instructions 770 include a controller module 772, calculation and decision module 774 and an alert module 776.

Calculation and decision module 774 may include instructions for operating the blood-accessing and micro-mixing sections 710, 720 and analyzing data generated by the blood-accessing and micro-mixing sections 710, 720 (e.g., by sensors thereof) to determine one or more hematological properties of blood or other information (e.g., health states) of a body of a wearer of the device 700, such as a blood glucose level at a number of points in time. Calculation and decision module 774 can additionally include instructions for analyzing the data to determine if a medical condition or other specified condition is indicated, or other analytical processes relating to the environment proximate to the device 700 (e.g., based on information generated by additional sensors of the device 700). In particular, the calculation and decision module 774 may include instructions for operating the first 710 and second 720 blood-accessing and micro-mixing sections to access blood (e.g., for operating resistive heating elements of the blood-accessing and micro-mixing sections 710, 720 to ignite propellant and drive respective needles into skin) at respective specified points in time (e.g., points in time while a wearer sleeps, points in time during the week).

The controller module 772 can also include instructions for operating a user interface 730. For example, controller module 772 may include instructions for displaying data collected by the blood-accessing and micro-mixing sections 710, 720 and analyzed by the calculation and decision module 774, or for displaying one or more alerts generated by the alert module 776. Controller module 772 may include instructions for displaying data related to a detected hematological property of accessed blood and/or a determined health state of a wearer. Further, controller module 772 may include instructions to execute certain functions based on inputs accepted by the user interface 730, such as inputs accepted by one or more buttons disposed on the user interface (e.g., to operate one or both of the blood-accessing and micro-mixing sections 710, 720 to access blood from a wearer and/or to detect one or more properties of the accessed blood in response to an input from the user).

Communication platform 735 may also be operated by instructions within the controller module 772, such as instructions for sending and/or receiving information via a wireless antenna, which may be disposed on or in the device 700. The communication interface 735 can optionally include one or more oscillators, mixers, frequency injectors, etc. to modulate and/or demodulate information on a carrier frequency to be transmitted and/or received by the antenna. In some examples, the device 700 is configured to indicate an output from the processor by modulating an impedance of the antenna in a manner that is perceivable by a remote server or other remote computing device.

The program instructions of the calculation and decision module 774 may, in some examples, be stored in a computer-readable medium and executed by a processor located external to the device 700. For example, the device 700 could be configured to collect certain data regarding hematological properties from the user and then transmit the data to a remote server, which may include a mobile device, a personal computer, the cloud, or any other remote system, for further processing.

The computer readable medium 760 may further contain other data or information, such as medical and health history of a user of the device 700, that may be useful in determining whether a medical condition or some other specified condition is indicated. Further, the computer readable medium 760 may contain data corresponding to certain physiological parameter baselines, above or below which a medical condition is indicated. The baselines may be pre-stored on the computer readable medium 760, may be transmitted from a remote source, such as a remote server, or may be generated by the calculation and decision module 774 itself. The calculation and decision module 774 may include instructions for generating individual baselines for the user of the device 700 based on data collected based on a certain number of blood samples accessed using blood-accessing and micro-mixing elements (e.g., 710, 720) of the device 700. Baselines may also be generated by a remote server and transmitted to the device 700 via communication interface 730. The calculation and decision module 774 may also, upon determining that a medical or other emergency condition is indicated, generate one or more recommendations for the user of the device 700 based, at least in part, on consultation of a clinical protocol. Such recommendations may alternatively be generated by the remote server and transmitted to the device 700.

In some examples, the collected hematological property data, baseline profiles, health state information input by device users and generated recommendations and clinical protocols may additionally be input to a cloud network and be made available for download by a user's physician. Trend and other analyses may also be performed on the collected data, such as hemodynamic property data and health state information, in the cloud computing network and be made available for download by physicians or clinicians.

Further, hematological property and health state data from individuals or populations of device users may be used by physicians or clinicians in monitoring efficacy of a drug or other treatment. For example, high-density, real-time data may be collected from a population of device users who are participating in a clinical study to assess the safety and efficacy of a developmental drug or therapy. Such data may also be used on an individual level to assess a particular wearer's response to a drug or therapy. Based on this data, a physician or clinician may be able to tailor a drug treatment to suit an individual's needs.

In response to a determination by the calculation and decision module 774 that a medical or other specified condition is indicated (e.g., that a wearer is hyperglycemic or hypoglycemic, based on a detected glucose level of blood accessed from the body of the wearer), the alert module 776 may generate an alert via the user interface 730. The alert may include a visual component, such as textual or graphical information displayed on a display, an auditory component (e.g., an alarm sound), and/or tactile component (e.g., a vibration). The textual information may include one or more recommendations, such as a recommendation that the user of the device contact a medical professional, deliver a dose of a pharmaceutical (e.g., insulin), seek immediate medical attention, or administer a medication.

V. Example Method

Figure 8:
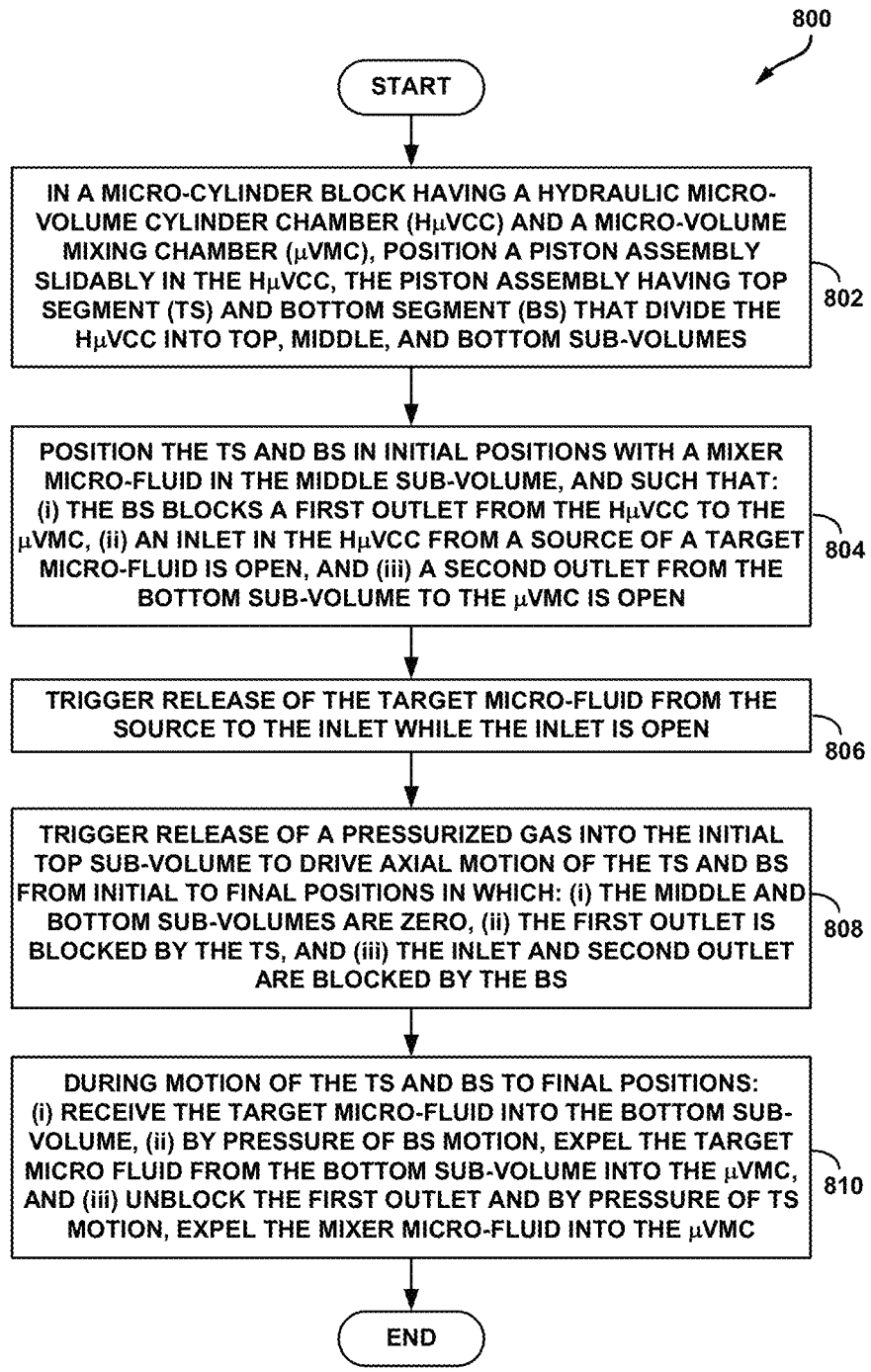
FIG. 8 is a flowchart of an example method.

FIG. 8 is a flowchart of an example method 800 for mixing two or more micro-fluids using an example micro-mixing device, such as devices 100, 200, or 300. The example micro-mixing device includes a micro-cylinder block housing a hydraulic micro-volume cylinder chamber (HµVCC) and a micro-volume mixing chamber (µVMC). In an example embodiment the HµVCC and µVMC may both have respective interior volumes in a range of 1-100 microliters.

In accordance with example embodiments, the micro-cylinder block includes: (i) a micro-fluid inlet having a micro-fluid inlet channel that provides a fluid connection from a source of a target micro-fluid to an inlet port in an interior wall of the HµVCC; (ii) a first micro-fluid outlet in the micro-cylinder block having a first micro-fluid outlet channel that provides a fluid connection from a first outlet port in the interior wall of the HµVCC to a first inlet opening in an interior wall of the µVMC; and (iii) a second micro-fluid outlet in the micro-cylinder block having a second micro-fluid outlet channel that provides a fluid connection from a second outlet port in the interior wall of the HµVCC to a second inlet opening in the interior wall of the µVMC.

As shown in FIG. 8, block 802 of the method 800 involves mounting or positioning a piston assembly slidably in the HµVCC for motion along an axial direction of the HµVCC. In accordance with example embodiments, the piston assembly includes (i) a top segment (TS) axially slidable from a TS initial position to a TS final position, and, beneath the TS, (ii) a bottom segment (BS) axially slidable from a BS initial position to a BS final position. In particular, the TS and BS divide the interior volume of the HµVCC into a top sub-volume extending above the TS to a top of the HµVCC, a middle sub-volume between the TS and BS, and a bottom sub-volume extending beneath the BS to a floor of the HµVCC. Further, the size and axial position of each sub-volume is adjustable according to the axial positions of the TS and BS within the HµVCC.

Block 804 of the method 800 involves positioning the TS in the TS initial position and positioning the BS in the BS initial position. In the initial position configuration, the middle sub-volume is filled with an initial mixer volume of a mixer micro-fluid that hydraulically links slidable motion of the TS and BS. In accordance with example embodiments, with the TS in the TS initial position and the BS in the BS initial position, certain operational aspects (possibly among others) are in place. Specifically: (i) all three sub-volumes are non-zero and positive, where each can be taken to define a respective initial sub-volume; (ii) the first outlet port is blocked by the BS, (iii) the inlet port is at least partially unobstructed, such that the inlet port is open to fluid flow from the source of the target micro-fluid into the bottom sub-volume, and (iv) the second outlet port is at least partially unobstructed, such that the second outlet port is open to fluid flow from the bottom sub-volume into the µVMC.

Block 806 of the method 800 involves triggering release of the target micro-fluid from the source of the target micro-fluid to the inlet port while the inlet port is open to fluid flow from the source of the target micro-fluid into the bottom sub-volume. That is, the inlet port being open is necessary condition for triggering release of the target micro-fluid.

Block 808 of the method 800 involves triggering release of pressurized gas into the initial top sub-volume so as to drive motion of the TS and BS from their respective TS and BS initial positions to their respective TS and BS final positions. In particular, delivery of pressurized gas into the top sub-volume is done while the TS is in the TS initial position and the BS is in the BS initial position, and with sufficient pressure force to drive axial motion of the TS and BS from their initial to final positions. In accordance with example embodiments, with the TS in the TS final position and the BS in the BS final position, certain further operational aspects (possibly among others) are in place. Specifically: (i) the middle sub-volume is zero; (ii) the first outlet port is blocked by the TS; (iii) the bottom sub-volume is substantially zero; and (iv) the inlet port and the second outlet port are blocked by the BS.

Block 808 of the method 800 involves actions during the motion of the TS and BS from their respective TS and BS initial positions to their respective TS and BS final positions. Specifically, actions during this motion include: receiving a target volume of the target micro-fluid into the bottom sub-volume through the inlet port; expelling the target volume of the target micro-fluid from the bottom sub-volume into the µVMC through the second outlet port by pressure of the BS moving toward the BS final position; unblocking the first outlet port by motion of the BS toward the BS final position, such that the first outlet port becomes at least partially unobstructed by the BS; and while the first outlet port is at least partially unobstructed by the BS, expelling the initial mixer volume of the mixer micro-fluid from the middle sub-volume into the µVMC through the first outlet port by pressure of the TS moving toward the BS.

In accordance with example embodiments, a relative timing between expelling the target micro-fluid from the bottom sub-volume into the µVMC and expelling the mixer micro-fluid from the middle sub-volume into the μVMC through the first outlet port can be adjustable. In particular, a relative timing (or ordering) can be adjustable according to at least one of: (i) relative axial thicknesses of the TS and the BS, (ii) relative axial positions of the first outlet and the second outlet, or (iii) relative timing between triggering release of the target micro-fluid from the source of the target micro-fluid and triggering delivery of pressurized gas into the top sub-volume. More particularly, expelling the target micro-fluid can be carried out before expelling the mixer micro-fluid, concurrently with expelling the mixer micro-fluid, or after expelling the mixer micro-fluid.

In accordance with example embodiments, the micro-cylinder block may be part of a micro-fluid mixing device that also includes a chemical analyzer. In such an arrangement, the method 800 can further entail analyzing one or more chemical properties of a micro-fluid mixture of a target volume of the target micro-fluid and a mixer volume of the mixer micro-fluid with the chemical analyzer. In an example aspect, the target volume may be no greater than the initial bottom sub-volume, and the mixer volume may be no greater than the initial mixer volume.

In further accordance with example embodiments, the μVMC may house an electrochemical sensor for measuring electrochemical properties of the mixer micro-fluid and of the target micro-fluid. More particularly, the mixer micro-fluid may be or contain a calibration fluid for the electrochemical sensor. The method 800 may then further entail calibrating measurements of the electrochemical sensor by exposing it to the mixer volume of the mixer fluid, and measuring electrochemical properties of the target volume of the target micro-fluid with the calibrated electrochemical sensor.

In accordance with example embodiments, the micro-cylinder block may be part of a micro-fluid mixing device that includes a blood-drawing subsystem, and the target micro-fluid could then be blood. In this arrangement, triggering release of the target micro-fluid from the source of the target micro-fluid to the inlet port may entail causing the blood-drawing subsystem to draw blood through adjacent dermal tissue. The micro-fluid mixing device may further include a chemical analyzer, and the mixer micro-fluid may be a diluent. The method 800 may then further entail using the chemical analyzer to analyze one or more chemical properties of a micro-fluid mixture of blood and diluent.

As a further example, the μVMC may house an electrochemical sensor for measuring electrochemical properties of the mixer micro-fluid and of the target micro-fluid, and the mixer micro-fluid may be a calibration fluid for the electrochemical sensor. The method 800 may then further entail calibrating measurements of the electrochemical sensor by exposing it to the mixer volume of the mixer fluid, and then measuring electrochemical properties of the target volume of the target micro-fluid with the calibrated electrochemical sensor.

In accordance with example embodiments, the source of pressurized gas may include a pre-pressurized gas cartridge with a triggered release valve gas-dynamically coupled into the top sub-volume. Triggering delivery of the pressurized gas into the top sub-volume may then entail releasing the pre-pressurized gas into the top sub-volume by releasing the valve. In an alternative arrangement, the source of pressurized gas may be or include a chemically-reactive gas generator having a trigger for initiating a gas-generating chemical reaction. The source of pressurized gas may also be gas-dynamically coupled into the top sub-volume. Triggering delivery of pressurized gas into the top sub-volume in this arrangement may entail initiating the gas-generating chemical reaction.

In a further arrangement, bottom sub-volume may contain a porous wicking material, such as a fibrous material or spongey material. Receiving the target volume of the target micro-fluid into the bottom sub-volume may then entail saturating the porous wicking material with the received target micro-fluid such that the received target micro-fluid becomes uniformly distributed throughout the bottom sub-volume.

The example method 800 illustrated in FIG. 8 is meant as an illustrative, non-limiting example. Additional or alternative elements of the method and additional or alternative components of the system are anticipated, as will be obvious to one skilled in the art.

VI. Conclusion

Where example embodiments involve information related to a person or a device of a person, the embodiments should be understood to include privacy controls. Such privacy controls include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Additionally, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:

1. A micro-fluid mixing device comprising:
a micro-cylinder block housing a hydraulic micro-volume cylinder chamber (HμVCC) and a micro-volume mixing chamber (μVMC);
a piston assembly slidably accommodated in the HμVCC for motion along an axial direction of the HμVCC, the piston assembly comprising (i) a top segment (TS) axially slidable from a TS initial position to a TS final position, and, beneath the TS, (ii) a bottom segment (BS) axially slidable from a BS initial position to a BS final position, wherein the TS and BS divide the interior volume of the HμVCC into a top sub-volume extending above the TS to a top of the HμVCC, a middle sub-volume between the TS and BS, and a bottom sub-volume extending beneath the BS to a floor of the HμVCC, the size and axial position of each sub-volume being adjustable according to the axial positions of the TS and BS within the HμVCC;
a source of pressurized gas having a triggered release mechanism and being dynamically coupled into the top sub-volume;
a micro-fluid inlet in the micro-cylinder block comprising a micro-fluid inlet channel providing a fluid connection from a source of a target micro-fluid to an inlet port in an interior wall of the HμVCC;
a first micro-fluid outlet in the micro-cylinder block comprising a first micro-fluid outlet channel providing a fluid connection from a first outlet port in the interior wall of the HμVCC to a first inlet opening in an interior wall of the μVMC; and
a second micro-fluid outlet in the micro-cylinder block comprising a second micro-fluid outlet channel providing a fluid connection from a second outlet port in the interior wall of the HμVCC to a second inlet opening in the interior wall of the μVMC,
wherein with the TS in the TS initial position and the BS in the BS initial position, at least: (i) all three sub-volumes are non-zero and positive, each defining a respective initial sub-volume, (ii) the middle sub-volume is filled with an initial mixer volume of mixer micro-fluid that hydraulically links slidable motion of the TS and BS, (iii) the first outlet port is blocked by the BS, and (iv) the inlet port and the second outlet port are both at least partially unobstructed, the inlet port being open to fluid flow from the source of the target micro-fluid into the bottom sub-volume, and the second outlet port being open to fluid flow from the bottom sub-volume into the μVMC,
wherein with the TS in at least one intermediate position between the TS initial position and the TS final position and the BS in at least one intermediate position between the BS initial position and the BS final position, at least: (i) the first outlet port is at least partially unobstructed, the first outlet port being open to fluid flow from the middle sub-volume to the μVMC,
wherein with the BS in at least one intermediate position between the BS initial position and the BS final position, at least: (i) the inlet port is blocked by the BS, and (ii) the second outlet port is at least partially unobstructed, the second outlet port being open to fluid flow from the bottom sub-volume to the μVMC,
wherein with the TS in the TS final position and the BS in the BS final position, at least: (i) the middle sub-volume is zero, (ii) the first outlet port is blocked by the TS, (iii) the bottom sub-volume is substantially zero, and (iv) the inlet port and the second outlet port are blocked by the BS,
and wherein the source of pressurized gas, upon triggered release into the top sub-volume, provides sufficient pressure force to drive motion of the TS and BS from the respective TS and BS initial positions to the respective TS and BS final positions.

2. The micro-fluid mixing device of claim 1, further comprising a shaft pin positioned axially within the HμVCC and extending normally through the piston assembly.

3. The micro-fluid mixing device of claim 1, wherein the source of the target micro-fluid comprises a triggered actuator for releasing the target micro-fluid, wherein the inlet port being open to fluid flow from the source of the target micro-fluid into the bottom sub-volume is a necessary condition for triggering the actuator to release the target micro-fluid.

4. The micro-fluid mixing device of claim 1, further comprising a chemical analyzer for analyzing one or more chemical properties of a micro-fluid mixture of a target volume of the target micro-fluid and a mixer volume of the mixer micro-fluid, wherein the target volume is no greater than the initial bottom sub-volume, and the mixer volume is no greater than the initial mixer volume.

5. The micro-fluid mixing device of claim 4, wherein the chemical analyzer is housed in the μVMC.

6. The micro-fluid mixing device of claim 4, further comprising a third micro-fluid outlet in the micro-cylinder block comprising a third micro-fluid outlet channel providing a fluid connection from a third outlet port in an interior boundary surface of the μVMC to the chemical analyzer.

7. The micro-fluid mixing device of claim 1, further comprising an electrochemical sensor housed in the μVMC for measuring electrochemical properties of the mixer micro-fluid and of the target micro-fluid,
wherein measurements by the electrochemical sensor are calibrated by measuring electrochemical properties of a calibration fluid,
and wherein the mixer micro-fluid comprises the calibration fluid.

8. The micro-fluid mixing device of claim 1, wherein the target micro-fluid is blood,
and wherein the source of a target micro-fluid comprises a blood-drawing subsystem of the micro-fluid mixing device.

9. The micro-fluid mixing device of claim 8, wherein the mixer micro-fluid comprises a diluent.

10. The micro-fluid mixing device of claim 8, further comprising a chemical analyzer for analyzing one or more chemical properties of blood.

11. The micro-fluid mixing device of claim 8, wherein the mixer micro-fluid comprises a calibration fluid for calibrating an electrochemical sensor housed in the μVMC for measuring electrochemical properties of blood.

12. The micro-fluid mixing device of claim 1, wherein the source of pressurized gas comprises a pre-pressurized gas cartridge with a triggered release valve.

13. The micro-fluid mixing device of claim 1, wherein the source of pressurized gas comprises a chemically-reactive gas generator having a trigger for initiating a gas-generating chemical reaction.

14. The micro-fluid mixing device of claim 1, further comprising a compressible wicking material in the bottom sub-volume for uniformly distributing target micro-fluid throughout the bottom sub-volume.

15. The micro-fluid mixing device of claim 1, further comprising a device assembly housing one or more micro-cylinder blocks, each including a respective piston assembly, a respective source of pressurized gas, and a respective initial volume of the mixer micro-fluid, and each having a respective source of the target micro-fluid.

16. The micro-fluid mixing device of claim 15, wherein the device assembly is one of a hand-held device or a wearable device.

17. The micro-fluid mixing device of claim 15, wherein the one or more micro-cylinder blocks comprises an array of multiple micro-cylinder blocks.

18. A method employing a micro-cylinder block housing a hydraulic micro-volume cylinder chamber (HµVCC) and a micro-volume mixing chamber (µVMC), the method comprising:
  mounting a piston assembly slidably in the HµVCC for motion along an axial direction of the HµVCC, wherein the piston assembly comprises (i) a top segment (TS) axially slidable from a TS initial position to a TS final position, and, beneath the TS, (ii) a bottom segment (BS) axially slidable from a BS initial position to a BS final position, and wherein the TS and BS divide the interior volume of the HµVCC into a top sub-volume extending above the TS to a top of the HµVCC, a middle sub-volume between the TS and BS, and a bottom sub-volume extending beneath the BS to a floor of the HµVCC, the size and axial position of each sub-volume being adjustable according to the axial positions of the TS and BS within the HµVCC;
  positioning the TS in the TS initial position and the BS in the BS initial position with the middle sub-volume filled with an initial mixer volume of mixer micro-fluid that hydraulically links slidable motion of the TS and BS, wherein with the TS in the TS initial position and the BS in the BS initial position, at least: (i) all three sub-volumes are non-zero and positive, each defining a respective initial sub-volume, (ii) a first outlet port in an interior wall of the HµVCC to a first fluid connection to the µVMC is blocked by the BS, (iii) an inlet port in the interior wall of the HµVCC from a source of a target micro-fluid is at least partially unobstructed, such that the inlet port is open to fluid flow from the source of the target micro-fluid into the bottom sub-volume, and (iv) a second outlet port in the interior wall of the HµVCC to a second fluid connection to the µVMC is at least partially unobstructed, such that the second outlet port is open to fluid flow from the bottom sub-volume into the µVMC;
  triggering release of the target micro-fluid from the source of the target micro-fluid to the inlet port while the inlet port is open to fluid flow from the source of the target micro-fluid into the bottom sub-volume;
  while the TS is in the TS initial position and the BS is in the BS initial position, triggering delivery of pressurized gas into the top sub-volume with sufficient pressure force to drive motion of the TS and BS from their respective TS and BS initial positions to their respective TS and BS final positions, wherein with the TS in the TS final position and the BS in the BS final position, at least: (i) the middle sub-volume is zero, (ii) the first outlet port is blocked by the TS, (iii) the bottom sub-volume is substantially zero, and (iv) the inlet port and the second outlet port are blocked by the BS;
  during the motion of the TS and BS from their respective TS and BS initial positions to their respective TS and BS final positions, receiving a target volume of the target micro-fluid into the bottom sub-volume through the inlet port;
  during the motion of the TS and BS from their respective TS and BS initial positions to their respective TS and BS final positions, expelling the target volume of the target micro-fluid from the bottom sub-volume into the µVMC through the second outlet port by pressure of the BS moving toward the BS final position;
  during the motion of the TS and BS from their respective TS and BS initial positions to their respective TS and BS final positions, unblocking the first outlet port by motion of the BS toward the BS final position, such that the first outlet port becomes at least partially unobstructed by the BS; and
  during the motion of the TS and BS from their respective TS and BS initial positions to their respective TS and BS final positions, while the first outlet port is at least partially unobstructed by the BS, expelling the initial mixer volume of the mixer micro-fluid from the middle sub-volume into the µVMC through the first outlet port by pressure of the TS moving toward the BS.

19. The method of claim 18, wherein a relative timing between expelling the target volume of the target micro-fluid from the bottom sub-volume into the µVMC through the second outlet port and expelling the initial mixer volume of the mixer micro-fluid from the middle sub-volume into the µVMC through the first outlet port is adjustable according to at least one of: (i) relative axial thicknesses of the TS and the BS, (ii) relative axial positions of the first outlet and the second outlet, or (iii) relative timing between triggering release of the target micro-fluid from the source of the target micro-fluid to the inlet port and triggering delivery of pressurized gas into the top sub-volume.

20. The method of claim 18, wherein expelling the target volume of the target micro-fluid from the bottom sub-volume into the µVMC through the second outlet port is carried out one of: (i) before expelling the initial mixer volume of the mixer micro-fluid from the middle sub-volume into the µVMC through the first outlet port, or (ii) concurrently with expelling the initial mixer volume of the mixer micro-fluid from the middle sub-volume into the µVMC through the first outlet port.

21. The method of claim 18, wherein expelling the target volume of the target micro-fluid from the bottom sub-volume into the µVMC through the second outlet port is carried out after expelling the initial mixer volume of the mixer micro-fluid from the middle sub-volume into the µVMC through the first outlet port.

22. The method of claim 20, wherein the micro-cylinder block is part of a micro-fluid mixing device that further includes a chemical analyzer,
  and wherein the method further comprises analyzing one or more chemical properties of a micro-fluid mixture of a target volume of the target micro-fluid and a mixer volume of the mixer micro-fluid with the chemical analyzer, wherein the target volume is no greater than the initial bottom sub-volume, and the mixer volume is no greater than the initial mixer volume.

23. The method of claim 21, wherein the µVMC houses an electrochemical sensor for measuring electrochemical properties of the mixer micro-fluid and of the target micro-fluid,
  wherein the mixer micro-fluid comprises a calibration fluid for the electrochemical sensor, and wherein the method further comprises:
calibrating measurements of the electrochemical sensor by exposing it to the mixer volume of the mixer fluid; and
measuring electrochemical properties of the target volume of the target micro-fluid with the calibrated electrochemical sensor.

24. The method of claim 18, wherein the target micro-fluid is blood,
wherein the micro-cylinder block is part of a micro-fluid mixing device that further includes a blood-drawing subsystem,
and wherein triggering release of the target micro-fluid from the source of the target micro-fluid to the inlet port comprises causing the blood-drawing subsystem to draw blood through adjacent dermal tissue.

25. The method of claim 24, wherein the mixer micro-fluid comprises a diluent,
wherein the micro-fluid mixing device further includes a chemical analyzer,
and wherein the method further comprises analyzing, with the chemical analyzer, one or more chemical properties of a micro-fluid mixture of blood expelled from the bottom sub-volume into the µVMC through the second outlet port and diluent expelled from the middle sub-volume into the µVMC through the first outlet port.

26. The method of claim 24, wherein the µVMC houses an electrochemical sensor for measuring electrochemical properties of fluids,
wherein the mixer micro-fluid comprises a calibration fluid for the electrochemical sensor,
and wherein the method further comprises:
calibrating measurements of the electrochemical sensor by exposing it to the mixer fluid expelled from the middle sub-volume into the µVMC through the first outlet port; and
measuring, with the calibrated electrochemical sensor, electrochemical properties of blood expelled from the bottom sub-volume into the µVMC through the second outlet port.

27. The method of claim 18, wherein the source of pressurized gas comprises a pre-pressurized gas cartridge with a triggered release valve gas-dynamically coupled into the top sub-volume,
and wherein triggering delivery of pressurized gas into the top sub-volume comprises releasing the pre-pressurized gas into the top sub-volume by releasing the valve.

28. The method of claim 18, wherein the source of pressurized gas comprises a chemically-reactive gas generator having a trigger for initiating a gas-generating chemical reaction, and being gas-dynamically coupled into the top sub-volume,
and wherein triggering delivery of pressurized gas into the top sub-volume comprises initiating the gas-generating chemical reaction.

29. The method of claim 18, wherein bottom sub-volume contains a porous wicking material,
and wherein receiving a target volume of the target micro-fluid into the bottom sub-volume through the inlet port comprises saturating the porous wicking material with the received target micro-fluid such that the received target micro-fluid becomes uniformly distributed throughout the bottom sub-volume.

30. A micro-fluid mixing device comprising:
a micro-vessel block housing both a plurality of micro-volume fluid chambers (µVFCs) and a micro-volume mixing chamber (µVMC);
a respective micro-fluid outlet channel between each respective µVFC and the µVMC, each respective micro-fluid outlet channel providing a respective fluid connection from a respective outlet port in the respective µVFC to a respective inlet opening in the µVMC;
a respective deformable interior surface portion in each respective µVFC for reducing a respective interior volume of the respective µVFC from a respective initial volume to a smaller, respective final volume according to deformation of the respective deformable interior surface portion from a respective initial position to a respective final position;
a respective micro-fluid filling the respective initial volume of each respective µVFC; and
a source of pressurized gas having a triggered release mechanism and being dynamically coupled to an exterior surface of each respective deformable interior surface portion, and comprising a source of sufficient pressure force for expelling the respective micro-fluid from each respective µVFC into the µVMC via the respective micro-fluid outlet channels by deforming each respective deformable interior surface portion from its respective initial position to its respective final position.

31. The micro-fluid mixing device of claim 30, further comprising a micro-fluid inlet channel between a source of a target micro-fluid and at least one µVMC of the plurality, the micro-fluid inlet channel providing a fluid connection from the source of the target micro-fluid to the at least one µVFC via a respective inlet opening in the at least one µVMC, and the source of the target micro-fluid being a source of the micro-fluid filling the initial volume of the at least one µVFC.

32. The micro-fluid mixing device of claim 30, further comprising a chemical analyzer for analyzing one or more chemical properties of a micro-fluid mixture of the respective micro-fluids.

33. The micro-fluid mixing device of claim 30, further comprising an electrochemical sensor housed in the µVMC for measuring electrochemical properties of fluids,
wherein measurements by the electrochemical sensor are calibrated by measuring electrochemical properties of a calibration fluid,
and wherein one of the respective micro-fluids comprises the calibration fluid.

34. The micro-fluid mixing device of claim 31, wherein the target micro-fluid is blood,
and wherein the source of a target micro-fluid comprises a blood-drawing subsystem of the micro-fluid mixing device.

35. The micro-fluid mixing device of claim 34, wherein the mixer micro-fluid comprises a diluent.

36. The micro-fluid mixing device of claim 34, further comprising a chemical analyzer for analyzing one or more chemical properties of blood.

37. The micro-fluid mixing device of claim 30, wherein the source of pressurized gas is one of: a pre-pressurized gas cartridge with a triggered release valve, or a chemically-reactive gas generator having a trigger for initiating a gas-generating chemical reaction.

38. The micro-fluid mixing device of claim 30, further comprising a respective coupling between the triggered released mechanism and the exterior surface of each respective deformable interior surface portion for driving deformation of each respective deformable interior surface portion either: (i) concurrently, or (ii) sequentially.

39. The micro-fluid mixing device of claim 30, further comprising a device assembly housing one or more micro-vessel blocks, each including a respective source of pressurized gas, and each having a respective source of the target micro-fluid, wherein the device assembly is one of a hand-held device or a wearable device.

\* \* \* \* \*